United States Patent
Chen et al.

(10) Patent No.: US 6,747,735 B2
(45) Date of Patent: Jun. 8, 2004

(54) MULTIPLEX COHERENT RAMAN SPECTROSCOPY DETECTOR AND METHOD

(75) Inventors: Peter Chen, Atlanta, GA (US);
Candace C. Joyner, Austell, GA (US);
Sheena T. Patrick, Durham, NC (US);
Dean R. Guyer, Bellevue, WA (US)

(73) Assignee: Spelman College, Atlanta, GA (US)

( * ) Notice: Subject to any disclaimer, the term of this patent is extended or adjusted under 35 U.S.C. 154(b) by 0 days.

(21) Appl. No.: 10/450,403

(22) PCT Filed: Dec. 13, 2001

(86) PCT No.: PCT/US01/45852

§ 371 (c)(1),
(2), (4) Date: Jun. 13, 2003

(87) PCT Pub. No.: WO02/48660

PCT Pub. Date: Jun. 20, 2002

(65) Prior Publication Data

US 2004/0042006 A1 Mar. 4, 2004

Related U.S. Application Data

(60) Provisional application No. 60/254,926, filed on Dec. 13, 2000.

(51) Int. Cl.[7] .............................. G01J 3/44; G01N 21/65
(52) U.S. Cl. ....................................................... 356/301
(58) Field of Search ......................................... 356/301

(56) References Cited

U.S. PATENT DOCUMENTS

| | | | |
|---|---|---|---|
| 4,529,943 A | 7/1985 | George et al. | 356/301 |
| 4,573,792 A | 3/1986 | Kajiyama et al. | 372/3 |
| 4,599,725 A | 7/1986 | George | 372/3 |

*Primary Examiner*—F. L. Evans
(74) *Attorney, Agent, or Firm*—Fitzpatrick, Cella, Harper & Scinto

(57) ABSTRACT

A multiplex coherent Raman spectrometer (10) and spectroscopy method rapidly detects and identifies individual components of a chemical mixture separated by a separation technique, such as gas chromatography. The spectrometer (10) and method accurately identify a variety of compounds because they produce the entire gas phase vibrational Raman spectrum of the unknown gas. This is accomplished by tilting a Raman cell (20) to produce a high-intensity, backward-stimulated, coherent Raman beam of 683 nm, which drives a degenerate optical parametric oscillator (28) to produce a broadband beam of 1100–1700 nm covering a range of more than 3000 wavenumber. This broadband beam is combined with a narrowband beam of 532 nm having a bandwidth of 0.003 wavenumbers and focused into a heated windowless cell (38) that receives gases separated by a gas chromatograph (40). The Raman radiation scattered from these gases is filtered and sent to a monochromator (50) with multichannel detection.

54 Claims, 5 Drawing Sheets

MULTIPLEX COHERENT RAMAN SPECTROSCOPY DETECTOR AND METHOD

CROSS-REFERENCE TO RELATED PROVISIONAL APPLICATION

This application claims the benefit of the filing date of provisional application no. 60/254,926, filed Dec. 13, 2000.

STATEMENT REGARDING FEDERALLY SPONSORED RESEARCH

This invention was made with Government support under National Science Foundation grant CHE-9702087, NASA Faculty Awards for Research grant NAG3-1974 and NASA grant NCC3-758, and Department of Energy grant DE-FG01-96EW13219. The Government has certain rights in this invention.

BACKGROUND OF THE INVENTION

1. Field of the Invention

The present invention relates to a multiplex coherent Raman spectroscopic detector and method for generating and detecting coherent Raman radiation from a sample. More specifically, the present invention relates to a multiplex coherent Raman radiation detector and method for generating and detecting coherent Raman radiation scattered by the components of an unknown sample and using the coherent Raman radiation to determine the identity of the sample's constituents.

The present invention also relates to an apparatus and method for illuminating a gaseous sample with broadband light with a continuous range of more than 3000 wavenumbers and with a narrowband light having a bandwidth of less than 1 wavenumber, and preferably about 0.003 wavenumbers to produce the entire gas phase vibrational Raman spectrum of the sample, thereby permitting accurate identification of the sample.

In addition, the present invention relates to an apparatus and method for increasing the intensity of the backward-propagating, phase-conjugate, coherent Raman radiation produced by a Raman cell. Moreover, the present invention also relates to an apparatus and method for using this enhanced, backward-propagating, phase-conjugate, coherent Raman radiation to drive a device capable of producing broadband light of more than 3000 wavenumbers.

2. Description of Related Art

In many fields, such as scientific research, industrial research, and forensics, it is often necessary to identify the chemical composition of an unknown sample. This task is often performed by first isolating the different compounds in the sample, and then applying an identification technique to each isolated compound. One standard method for isolating unknown compounds is called gas chromatography, where the unknown sample is transformed into a gas, if not already in the gaseous state, and the various compounds in the gas are separated due to their differing gaseous properties, such as polarity. Once the compounds are isolated, they may be identified. The simplest way to identify the compounds is by noting the time it takes for each compound to pass through the gas chromatograph, since different compounds take different amounts of time to do so. But this method is limited to samples where much is known about the components. A more powerful method for identifying isolated compounds examines the intensity of different wavelengths of light emitted, transmitted, reflected, or scattered by the compound. This technique, called spectroscopy, works if each compound emits, transmits, reflects, or scatters light differently and if the spectroscopic instrument has sufficient spectral resolution to detect these differences. More specifically, different chemical compounds emit, transmit, reflect, or scatter different wavelengths of light with differing intensities. A graph or picture of such data is called the spectrum of that compound. Different types of spectroscopy reproduce the spectrum of a compound over different wavelengths and/or under different conditions. If the type of spectroscopy used provides a unique spectrum for each chemical compound, an unknown compound can be identified by producing its spectrum (for example, by illuminating the compound and measuring the light reflected, scattered, or emitted therefrom) and comparing its spectrum with the spectra of known compounds. As a result, gas chromatographs, which isolate compounds from a sample, are often used with spectrometers, which identify the compounds once they are isolated.

One popular type of spectroscopy detector used with gas chromatographs requires the gas isolated by the gas chromatograph to be embedded in or condensed onto a substrate before spectroscopic examination. Such detectors provide advantages, such as low detection limits, but are complicated because they require the isolated gas to be condensed, trapped, or adsorbed onto a substrate. In addition, such detectors suffer from unwanted effects such as nearest-neighbor effects, sample decomposition, and a slow detection speed. As a result, detectors that operate "on the fly" with little or no sample modification are often faster and freer from unwanted effects.

One type of frequently-used "on the fly" spectroscopy is infrared spectroscopy. But infrared spectroscopy is sometimes unable to accurately determine the identity of an unknown sample because certain characteristics of some samples (i.e., those with spectra that are highly state-(phase) dependent and those that produce strong rotational side bands in the infrared light absorbed by the sample that cause a loss of spectral resolution) reduce its accuracy. Furthermore, certain molecules, such as homonuclear diatomics, have no infrared spectrum, and optical components designed to direct and process the infrared light used in an infrared spectrometer are often inferior to the optical components designed for use in the visible spectrum.

A type of spectroscopy that is less susceptible to these problems is called Raman spectroscopy. In this type of spectroscopy, light in the visible wavelength region or the near-visible wavelength region is projected onto a sample and a small fraction of this light is scattered in all directions by the sample and is measured. The light is scattered because the molecules of the sample inelastically scatter the light due to the vibrational or rotational motions in the molecules of the sample. Such scattered light is of two types: light whose wavelength is not shifted, which is called Rayleigh scattering, and light whose wavelength is shifted, which is called Raman scattering. The Raman scattered light is much less intense than the Rayleigh scattered light. Since the Raman scattered light is scattered and shifted in wavelength because of the vibration of molecules of the sample, a graph of the Raman scattered light from a sample is called the vibrational Raman spectrum of the sample and provides information about the internal vibrational motion of the molecules of the sample. Moreover, the entire vibrational Raman spectrum of each compound (which is approximately 3000 wavenumbers wide) is unique to that compound. As a result, unknown compounds can be identified by their vibrational Raman spectrum. But, the intensity of the Raman spectrum must be sufficiently strong to be detected by currently-developed detectors with a high signal-to-noise ratio, and the entire Raman vibrational spectrum, covering a range of at least 3000 wavenumbers (indicating a large number of wavelengths of light are measured) must be produced. If only a partial Raman vibrational spectrum is produced, the identity of the compound may not be determined with high accuracy, since many compounds can share the same partial Raman vibrational spectrum. When Raman spectroscopy is used to detect gases, such as those isolated by a gas chromatograph, it is called gas phase Raman spectroscopy.

Gas phase Raman spectroscopy provides several advantages over gas phase infrared spectroscopy. First, Raman spectroscopy is less susceptible to phase transitions in the sample and to unwanted broadening of scattered or absorbed light due to rotational sidebands, so species identification may be more accurate using Raman spectroscopy. Second, Raman spectroscopy can be used to identify more types of molecules than infrared spectroscopy, since certain molecules do not appear in infrared spectroscopy, while all molecules will appear in Raman spectroscopy. Third, several advanced techniques are available with Raman spectroscopy that improve its accuracy and generate additional, valuable data not available in infrared spectroscopy, including resonance Raman spectroscopy, surface enhanced Raman spectroscopy, and coherent Raman spectroscopy. Finally, the optical components commercially for use in the visible region are often superior to those available for use in the infrared region. For example, extremely sensitive and rapid multichannel detectors are available in the visible region but not in the infrared region.

But gas phase Raman spectroscopy suffers its own problems. The density of molecules in the gaseous sample is so low that long collection times (minutes or hours) are needed in order to generate Raman spectra. This problem precludes the use of conventional Raman spectroscopy as an on-the-fly detector for gas chromatography, since in gas chromatography, different gases emerge from the gas chromatograph every few minutes, seconds, or less.

In order to overcome this problem, Roth and Kiefer, in "Surface-Enhanced Raman Spectroscopy as a Detection Method in Gas Chromatography," Applied Spectroscopy vol. 48, 1994, 1193–1195, explored the potential use of surface enhanced Raman spectroscopy (SERS). Surface enhancement can be used to increase the strength of the Raman signal, thereby reducing the time required to obtain spectra. Later, Carron and Kennedy published the first paper showing actual chromatograms using a SERS detector in "Molecular-Specific Chromatographic Detector Using Modified SERS Substrates," Analytical Chemistry vol. 67, 1995, 3353–3356. Their method requires that the sample be trapped onto a substrate that attracts specific molecules based on their function groups and enhances them. This method offers high sensitivity and specificity. But it also suffers important disadvantages including the domination of the spectra by the substrate instead of the sample, the lack of universality of the technique (not all molecules will strongly adsorb onto a given substrate, and not all molecules will be enhanced), the frequent replacement of the substrate, and the possible decomposition of the sample or possible change of the sample upon adsorption onto the substrate.

To solve these problems with gas phase Raman spectroscopy, coherent Raman spectroscopy was developed in the early 1960s. Unlike conventional Raman spectroscopy and SERS, coherent Raman spectroscopy uses two or more pulsed lasers having sufficiently high peak intensities to cause a certain nonlinear optical effect in the sample that generates an intense, coherent beam in one direction. In contrast, in conventional Raman spectroscopy and in surface enhanced Raman spectroscopy, the signal is weakly scattered in all directions. This technique is described in "Multiplex Coherent Anti-Stokes Raman Spectroscopy by use of a Nearly Degenerate Broadband Optical Parametric Oscillator", Applied Optics, vol. 38, no. 27, pp. 5894–5898, Sep. 20, 1999 by Peter C. Chen, Candace C. Joyner, and Michael Burns-Kaurin, and "Improved Scanning Range for Coherent Anti-Stokes Raman Spectroscopy Using A Tunable Optical Parametric Oscillator", Analytical Chemistry, col. 68, no. 17, pp. 3068–3071, Sep. 1, 1996 by Peter Chen, both of which are incorporated by reference herein.

Coherent Raman spectroscopy is of two types—scanned coherent Raman spectroscopy and multiplex coherent Raman spectroscopy. Scanned coherent Raman spectroscopy uses narrowband tunable lasers. This method gradually changes the frequency of one or more laser beams aimed at a sample, while using equipment to monitor the size of a coherent Raman beam produced by the sample when irradiated by the frequency-changing laser beams. But with this approach, the length of time required to generate a single spectrum is long. In contrast, multiplex coherent Raman spectroscopy, which uses a combination of narrowband and broadband lasers, allows data to be generated very quickly (in as little as one or a few laser pulses). In the past, a primary limitation of the multiplex technique has been that the bandwidth of the lasers has not been suitable to cover the entire vibrational spectrum with high spectral resolution. As a result, it has not been possible to achieve highly accurate identification of all samples, since the entire vibrational Raman spectrum could not be produced with high spectral resolution.

Thus, there is a need for a multiplex coherent Raman spectrometer and multiplex coherent Raman spectroscopy method that can rapidly produce a vibrational Raman spectrum of a sample so that it covers the entire vibrational region with high spectral resolution, thereby improving the accuracy of sample identification. More specifically, there is a need for a multiplex coherent Raman spectrometer and spectroscopy method that can rapidly produce the entire vibrational Raman spectrum of approximately 3000 wavenumbers with sub-wavenumber resolution, thereby permitting highly accurate sample identification.

SUMMARY OF THE INVENTION

It is an object of the present invention to provide a multiplex coherent Raman spectroscopy detector and method that can produce a vibrational Raman spectrum of a sample covering more than 1000 wavenumbers, thereby increasing the accuracy of sample identification.

It is a further object of the present invention to illuminate a sample with broadband illumination of sufficient bandwidth that the sample will scatter coherent Raman light to produce a gas phase vibrational Raman spectrum of a sample covering more than 1000 wavenumbers, and preferably at least 3000 wavenumbers, thereby increasing the accuracy of sample identification.

It is still another object of the present invention to increase the intensity of backward-propagating, phase-conjugate, coherent Raman radiation produced by a Raman cell, and preferably to increase the intensity to provide a sufficiently strong input beam for pumping or driving an optical parametric oscillator to produce a substantially stable output.

According to one aspect, the present invention that achieves at least one of these objectives relates to a multiplex coherent Raman spectrometer and spectroscopy method for rapidly detecting and identifying individual components of a chemical mixture separated by a separations technique, such as gas chromatography. The spectrometer and method increase the accuracy with which a variety of compounds are identified because they comprise means, elements, and steps to produce a gas phase vibrational Raman spectrum of an unknown sample gas of more than 1000 wavenumbers, and preferably can do so rapidly (within one or a few laser pulses), with a high signal-to-noise ratio and without any gaps in the spectrum. Preferably, the spectrometer and method accurately identify a variety of compounds because they comprise means, elements, and steps to produce the entire gas phase vibrational Raman spectrum of an unknown sample gas covering at least 3000 wavenumbers.

According to another aspect, the present invention provides an element, a step, or means that drive a broadband-beam-producing device to simultaneously illuminate the sample with a stable broadband beam of more than 1000 wavenumbers bandwidth, and preferably more than 3000 wavenumbers bandwidth and with a narrowband beam of less than 1 wavenumber bandwidth and preferably about 0.003 wavenumbers bandwidth of sufficient intensity to produce a gas phase vibrational Raman spectrum of the sample of more than 1000 wavenumbers, and preferably more than 3000 with a spectral resolution of less than 1 wavenumber and preferably about 0.003 wavenumbers rapidly (within one or a few laser pulses) with a high signal-to-noise ratio and without any gaps in the spectrum.

The element, means, and step for driving such a broadband-beam producing device can comprise a hydrogen-filled Raman cell, tilted by less than 2.2 degrees with respect to an input beam entering the sample-filled Raman cell, to produce a high-intensity, backward-stimulated, coherent Raman beam of 683 nm. More generally, this element, means, or step will produce such a high-intensity, backward-stimulated, coherent Raman beam of 683 nm when the hydrogen-filled Raman cell is tilted with respect to an input beam up to (but not exceeding) the angle at which less than the entire input beam enters a hole in the hydrogen-filled Raman cell, so that the focal point of the entire input beam in the hydrogen-filled Raman cell collides with a side wall on the inside of the hydrogen-filled Raman cell, as shown in FIG. 5. This 683 nm beam can be used to drive a broadband-beam producing device, such as a degenerate optical parametric oscillator to produce a stable broadband beam of 1100–1700 nm that covers a continuous range of 3200 wavenumbers. This broadband beam is then combined with a narrowband beam of 532 nm having a bandwidth of less than 1 wavenumber and preferably about 0.003 wavenumbers and focused into a heated windowless sample-filled Raman cell that receives gases (i.e. the sample) separated by a gas chromatograph. When these gases are illuminated with the combined broadband and narrowband beams, they emit coherent Raman radiation. This Raman radiation is of sufficient intensity and bandwidth that when it is filtered and then sent to a monochromator with multi-channel detection, complete vibrational Raman spectra of at least 3000 wavenumbers is produced from one or a few laser pulses, without any gaps in the vibrational Raman spectra and with a high signal-to-noise ratio.

Other objects and features of the present invention will become more apparent upon consideration of the following detailed description of preferred embodiments taken in conjunction with the accompanying drawings.

DETAILED DESCRIPTION OF PREFERRED EMBODIMENTS

As used in this application, the term "coherent light source" refers to both laser and a device for producing coherent light, such as an optical parametric oscillator.

First Preferred Embodiment

Introduction

Figure 1:
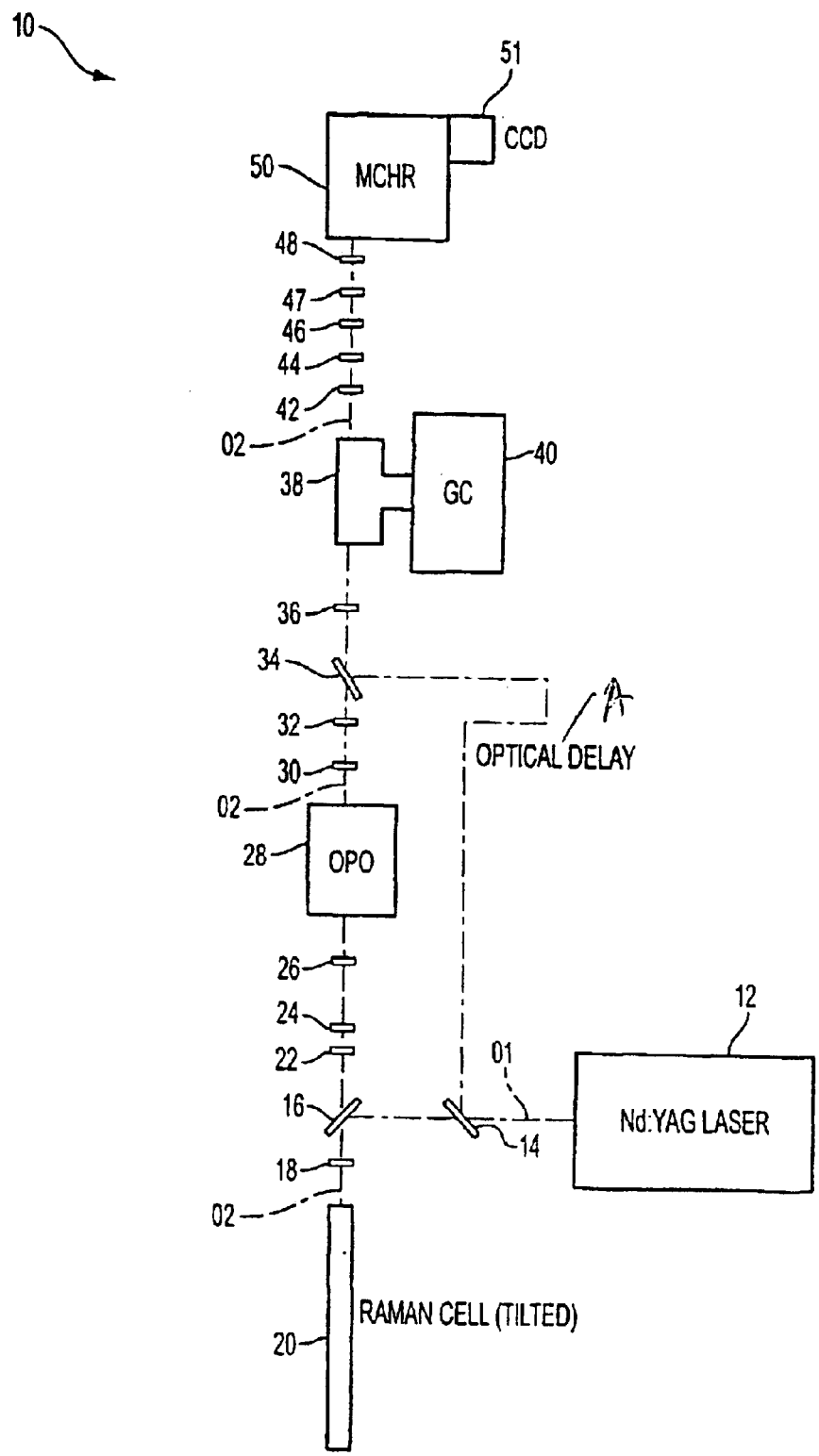
FIG. 1 is a schematic view of a first preferred embodiment of the Multiplex Coherent Raman Radiation Detector.

FIG. 1 is a schematic view of a first preferred embodiment of the multiplex coherent Raman detector 10. The detector 10 detects the Raman radiation emitted from an unknown gas and uses that Raman radiation to determine the identity of the gas with higher accuracy than has been possible before. This advantageous effect occurs because the FIG. 1 embodiment illuminates the unknown gas simultaneously with a broadband laser beam having a bandwidth of more than 3000 wavenumbers and a narrowband laser beam having a bandwidth of less than 1 wavenumber and preferably approximately 0.003 wavenumbers. This broadband and narrowband radiation, when scattered by an unknown gas, produces the entire gas phase vibrational Raman spectrum with a spectral resolution of less than 1 wavenumber and preferably approximately 0.003 wavenumbers without any gaps therein, which permits an accurate identification of the gas. As a result, the range-to-resolution ratio of this system, which provides a measure of the ability of the system to distinguish between similar but not identical chemical species, is 3000/0.003=1,000,000. The narrowband laser beam is produced by an injection-seeded, near transform-limited Nd:YAG laser 12. The broadband illumination is produced by an optical parametric oscillator 28. The optical parametric oscillator must be pumped by a sufficiently strong 683 nm beam to generate stable broadband radiation of sufficient intensity that the Raman radiation scattered by the unknown gas can be detected by a monochromator and a CCD. This task is accomplished by slightly tilting a hydrogen-filled Raman cell with respect to an incident 532 nm laser beam. Such tilting increases the intensity of the 683 nm laser beam produced by the Raman cell to the required degree.

Production of Broadband and Narrowband Light for Sample Illumination Producing and Splitting of Laser Beam The detector 10 comprises an injection seeded Nd:YAG laser 12 (manufactured by Spectraphysics, model no. GCR-230 laser with an EEO-355 option) that produces a second harmonic beam whose wavelength is 532 nm. This type of laser is a Q-switched nanosecond laser and because it is injection seeded, it produces a laser beam having a bandwidth of about 0.003 wavenumbers. The laser 12 has a 10 Hz repetition rate and the second harmonic beam produced thereby has an energy of about 200 mJ per 5 ns pulse. The second harmonic 532 nm beam is projected by the laser 12 along optical axis 01 to a wedge reflector 14. The wedge reflector 14 reflects a portion of the 532 nm beam (approximately 5 mJ) to a variety of optical elements (not shown) including a Pellin Broca prism that purify it and delay its arrival at a gas chromatograph, as will be discussed below. The remainder of the 532 nm beam passes through the wedge reflector 14 and is reflected by a dichroic mirror 16 (manufactured by CVI, model no. Y2-1025-45-UNP). The dichroic mirror 16 reflects 532 nm light and transmits 683 nm light. The dichroic mirror 16 reflects the 532 nm beam along optical axis 02 to a 0.5 m focal-length, plano-convex lens 18 (manufactured by Coherent, model no. 43-0546-000) that focuses the beam along optical axis 02 into a cylindrical, stainless steel Raman cell 20 filled with hydrogen. In response to receiving the focused 532 nm beam, the hydrogen-filled Raman cell 20 produces a backward-propagating, phase-conjugate, stimulated Raman-scattered 683 nm beam traveling back along the optical axis 02 toward the lens 18.

Producing a Broadband-light-production Driving Beam with a Raman Cell

The hydrogen-filled cylindrical Raman cell 20 is one meter in length, one inch in outer diameter, 0.75 inches in inner diameter, and is tilted approximately one degree with respect to the optical axis 02. Applicants have discovered that the tilting of the Raman cell increases the energy of the coherent Raman radiation by as much as four times as compared to the energy of the coherent Raman radiation produced by the hydrogen-filled Raman cell 20 without tilting. Thus, in this embodiment, the energy of the 683 nm beam produced by the hydrogen-filled Raman cell 20 can reach 130 mJ when the incident 532 nm beam is 340 mJ. More typically, the laser 12 produces a 532 nm beam whose energy when entering the hydrogen-filled Raman cell 20 is approximately 200 mJ, thereby producing a 683 nm beam of 70 mJ. This increased energy of the coherent Raman radiation produced by the hydrogen-filled Raman cell 20 is needed to generate a sufficiently strong broadband beam in the optical parametric oscillator (to be discussed below) that the Raman radiation produced in response to illuminating an unknown gas with the broadband beam has sufficient strength to be detected with a high signal-to-noise ratio when using a monochromator and a CCD (charge coupled device) and a computer. Without tilting, saturation of the Raman-scattering process within the hydrogen-filled Raman cell 20 limits the energy of the 683 nm pulse to about 30 mJ. In fact, at high 532 nm beam energies, saturation can cause the 683 nm output beam energy to slightly decrease as the 532 nm input beam energy is increased.

Advantageously, the quality of the 683 nm phase-conjugate beam produced by the hydrogen-filled Raman cell 20 is almost identical to that of the 532 nm beam, which is high due to the Gaussian optics used in the Nd:YAG 12. A high quality beam is a beam of a substantially circular cross-section of substantially uniform intensity throughout the area of the cross-section.

Disadvantageously, the length of the backward-propagating pulse of the 683 nm beam produced by the hydrogen-filled Raman cell 20 is much shorter than the pulse of the incident 532 nm beam. But this disadvantage is overcome in the present embodiment by creating a pulse train, using gas under high pressure in the hydrogen-filled Raman cell 20, such as at least 200 psi and preferably 400 psi of hydrogen, and by using an optical parametric oscillator of short cavity length of 5 inches or less, as will be discussed below. More generally, the length of the OPO 28 is such that the time required for the 683 nm beam to travel twice the cavity length of the OPO 28 is less than the pulse length of the 683 nm beam.

The hydrogen-filled Raman cell 20 projects the 683 nm phase conjugate beam along the optical axis 02 through the lens 18, which collimates and directs the beam through the dichroic mirror 16 to a telescope comprising a +175 mm focal-length, plano-convex lens 22 (manufactured by Edmund Scientific, model no. 32,866) and a —100 mm focal-length lens 24 (manufactured by Edmund Scientific, model no. 45,027), which together reduce the diameter of the 683 nm beam. The reduced-diameter 683 nm beam then travels along the optical axis 02 to a half-wave plate 26, which rotates the beam polarization to a vertical polarization before it enters a free-running optical parametric oscillator (OPO) 28. In response to receiving the 683 nm vertically-polarized beam, the OPO 28 produces a broadband beam of 1100–1700 nm covering a continuous range of over 3000 wavenumbers, and more specifically 3200 wavenumbers. Using a beam with this broad a bandwidth (in combination with a narrowband beam, as will be discussed below) permits the entire gas phase vibrational Raman spectrum of an unknown sample to be obtained rapidly, within 1 or a few laser pulses, without gaps and with a high signal-to-noise ratio, thereby permitting accurate identification of the sample.

Producing Broadband Illumination with an Optical Parametric Oscillator

Figure 2:
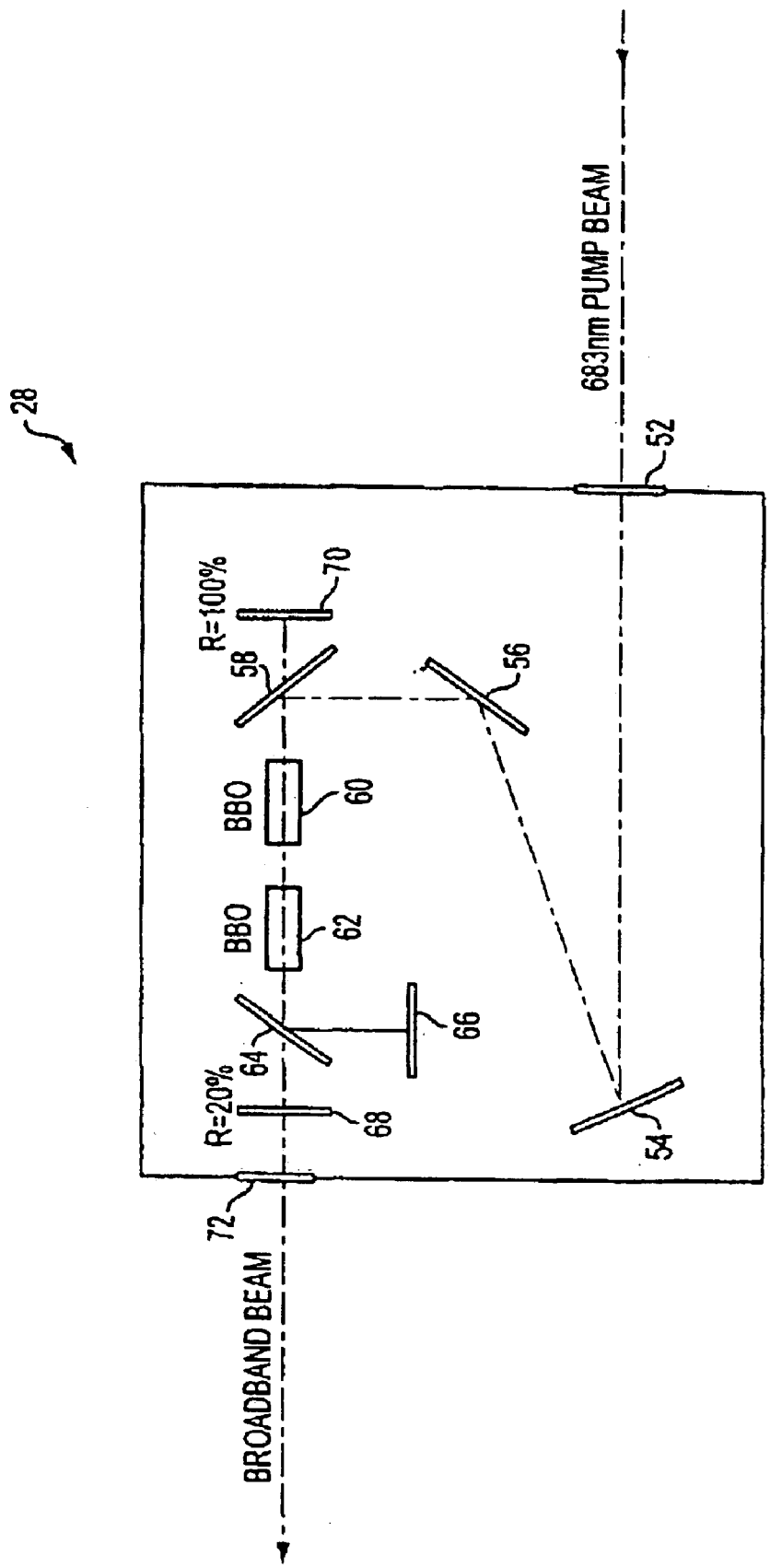
FIG. 2 is a schematic view of the optical parametric oscillator used in the Multiplex Coherent Raman Radiation Detector.

FIG. 2 shows the OPO 28. The OPO 28 comprises a window 52 receiving the reduced-diameter, vertically-polarized 683 nm beam from the half-wave plate 26. The OPO 28 also comprises a dichroic mirror 54 (manufactured by CVI, model no. TLM1-690-0-1037) for reflecting the 683 nm beam received by the window 52 to a mirror 56 (manufactured by CVI, model no. R1-1025-45-UNP). The mirror 56 reflects the 683 nm beam to an identical dichroic mirror 58 that reflects the 683 nm beam through two BBO (beta barium borate) crystals 60 and 62 cut for type I phase matching and that can be manually tilted. Each BBO crystal is manufactured by Casix, is 5 mm×5 mm×14 mm and cut at 22 degrees, and has two opposed, small faces that are coated with a single layer of magnesium fluoride, which is centered at 700 nm. The two crystals 60 and 62 are manually tilted so that they are tilted at similar angles, but in opposite directions and their angles are manually adjusted until they continuously emit broadband light in the range from 1100 nm to 1700 nm in response to receiving the 683 nm beam.

As a result, once the 683 nm light has initially passed through the crystals 60 and 62, two different types of light are projected from crystals 60 and 62—the 683 nm input beam and the 1100 nm–1700 nm output broadband beam. Both of these beams strike a dichroic mirror 64, identical to mirrors 56 and 58, which reflects the 683 nm beam and transmits the 1100 nm–1700 nm broadband beam.

The dichroic mirror 64 reflects the 683 nm beam to a mirror 66 identical to mirror 54, which, in turn, reflects the 683 nm beam back to the dichroic mirror 64 and out of the OPO 28 through the window 52 via the same path that this beam traveled through the OPO 28, i.e. back through the two crystals 60 and 62 to the dichroic mirror 58, which reflects the 683 nm beam to mirror 56, which, in turn, reflects the beam to mirror 54, where the 683 nm beam is reflected to window 52.

In contrast, the 1100 nm–1700 nm broadband beam, which is transmitted through the dichroic mirror 64, strikes a partially-reflecting mirror 68 (manufactured by CVI, model no. PR2-1350-1600-20-1037 or PR1-1319-20-1037) that functions as an output coupler. The mirror 68 permits 80% of the 1100 nm–1700 nm broadband beam to pass therethrough and out of the OPO 28 through a window 72. The mirror 68 also reflects 20% of the 1100 nm–1700 nm broadband beam back to the dichroic mirror 64, which transmits the 1100 nm–1700 nm broadband beam back through the two crystals 60 and 62 and then through the dichroic mirror 58 to a mirror 70 (manufactured by Newport, model no. 10D20ER.1). The mirror 70 reflects 100% of the 1100 nm–1700 nm broadband beam back through the dichroic mirror 58 and again through the two crystals 60 and 62 and the dichroic mirror 64 to the mirror 68, which again transmits 80% of the 1100 nm–1700 nm broadband beam out of the OPO 28 through the window 72 and reflects 20% of the 1100 nm–1700 nm broadband beam back through the crystals 60 and 62 toward the dichroic mirror 58 and the mirror 70, as noted above, where the process is continuously repeated, until the beam output from window 72 in response to a given pulse from the laser 12 diminishes to zero intensity.

In addition, the 1100 nm–1700 nm broadband beam is again generated anew as the 683 nm beam is reflected by the dichroic mirror 64 through the two crystals 60 and 62. In this case, the newly generated 1100 nm–1700 nm broadband beam is transmitted through the dichroic mirror 58 to the mirror 70, which reflects 100% of the 1100 nm–1700 nm broadband beam back through the dichroic mirror 58 and again through the two crystals 60 and 62 and the dichroic mirror 64 to the mirror 68, which transmits 80% of the 1100 nm–1700 nm broadband beam out of the OPO 28 through the window 72 and reflects 20% of the 1100 nm–1700 nm broadband beam back through the crystals 60 and 62 toward the dichroic mirror 58 and the mirror 70, where the process is continuously repeated, until the beam output from window 72 in response to a given pulse from the laser 12 diminishes to zero intensity.

As a result of this process, a 1100 nm–1700 nm broadband beam is output from the window 72 at 5–10 mJ per pulse.

The OPO 28 has an intensity threshold of 10–30 mJ per pulse, below which a 683 nm beam input into the OPO will not produce a 1100 nm–1700 broadband beam. The cell 20, when tilted 1 degree and in response to receiving a 200 mJ, 532 nm beam, produces a 683 nm beam of an intensity above this threshold of the OPO 28. But, if the OPO 28 is driven by an input 683 nm beam merely at this intensity threshold, it will produce an unstable 1100–1700 nm output beam. To produce a stable 1100–1700 nm output beam, the 683 nm input beam must be above this threshold by a substantial amount, for example, 50–100% above the threshold. When the cell 20 is tilted 1 degree in response to receiving a 200 mJ, 532 nm beam, the cell 20 produces a 683 nm beam whose intensity is above this threshold by the predetermined amount so as the drive the OPO 28 to produce a stable 1100 nm–1700 nm broadband beam.

Combining of Broadband and Narrowband Beams for Sample Illumination

Referring again to FIG. 1, the 1100 nm–1700 nm broadband beam emerging from the window 72 of the OPO 28 enters a filter 30 (manufactured by Schott Glass Technologies, model no. RG830), which filters out any visible ambient light. The 1100 nm–1700 nm broadband beam then enters a 0.5 m focal-length, plano-convex lens 32 (manufactured by Coherent, model no. 43-0546-000). The lens 32 collimates the broadband beam, which then strikes a dichroic mirror 34 (manufactured by CVI, model no. LWP-0-RUNP532-TUNP1000-2000). The dichroic mirror 34 permits the 1100 nm–1700 nm broadband beam to pass therethrough, since it transmits light of wavelengths between 1000 nm and 2000 nm. In addition, the dichroic mirror 34 receives the 532 nm beam from the laser 12 that has been reflected by the wedge reflector 14 and delayed (by optical elements that are not shown in FIG. 1) so as to arrive at the dichroic mirror 34 at the same time as the 1100 nm–1700 nm broadband beam collimated by the lens 32. The dichroic mirror 34 reflects the delayed 532 nm beam along the optical axis 02 at the same time that the 1100 nm–1700 nm broadband beam passes through the dichroic mirror 34 and also travels along optical axis 02. As a result, the 532 nm beam and the 1100 nm–1700 nm broadband beam are spatially and temporally overlapped as they travel from the dichroic mirror 34 along optical axis 02.

In an alternative embodiment of FIG. 1, the narrowband coherent beam that is combined with the broadband coherent beam at the dichroic mirror 34, originates with a second OPO (not shown) rather than with the laser 12. As a result, the reflected beam from the wedge reflector 14 is terminated by a beam block (not shown). In this alternative embodiment, there is provided a second OPO, having a tuning range from 220 nm to 1800 nm, which is driven by a second laser (not shown). The second OPO generates a narrowband coherent beam having a bandwidth of 0.2 wavenumbers. Optical elements (not shown) direct the narrowband coherent beam from the second OPO to the dichroic mirror 34, which is different from the mirror 34 in FIG. 1 in that it is designed to reflect the narrowband coherent beam from the second OPO and combines this narrowband coherent beam from the second OPO with the broadband coherent beam transmitted through the lens 32 so as to spatially and temporally overlap these two beams as they travel from the mirror 34 along optical axis 02. In this alternative embodiment, all the other elements are the same as in FIG. 1.

In both the embodiment shown in FIG. 1, and the alternative embodiment of FIG. 1, the combined beams will be used to illuminate an unknown sample gas to create a multiplex coherent Raman beam. The method of creating a multiplex coherent Raman beam using a single narrowband laser beam and broadband light resembles a technique known as dual broadband CARS that uses two broadband dye lasers, a method developed by Eckbreth and Anderson, in "Dual broadband CARS for simultaneous, multiple species measurements", Applied Optics vol. 24, 1985, 2731–2736. Here, a single broadband OPO takes the place of the two broadband dye lasers used by Eckbreth and Anderson. In addition, here the signal is detected over a range of 450–530 nm. The use of this approach permits high resolution spectra to be generated without gaps, which may not be the case using other multiplex methods.

Illuminating an Unknown Sample with Narrowband and Broadband Light

The two overlapping beams then pass through an 8 inch focal-length, plano-convex lens 36 (manufactured by Edmund Scientific, model no. 45,152), which focuses the two overlapping beams at a point on optical axis 02 in a heated sample-filled Raman cell 38 that receives a stream of gases (i.e. the unknown sample whose identity is to be determined by detector 10) from a gas chromatograph 40 (manufactured by Gow Mac, model no. 400). The two overlapping beams are then scattered by the unknown sample gas to produce coherent Raman radiation, whose spectrum will be detected to determine the identity of the gas. Lens 32 ensures that the lens 36 focuses the two overlapping beams at the same point on optical axis 02. This use of overlapping narrowband and broadband beams to illuminate a sample to produce spectrally broad coherent Raman radiation is known as multiplex coherent Raman scattering and is necessary to produce coherent Raman spectra rapidly (at 10 Hz, the repetition rate of laser 12). By this arrangement, a Raman spectrum can be produced during one or two laser pulses. And since the repetition rate of the laser 12 is 10 Hz, a new Raman spectrum can be produced every 1/10 of a second, the time between laser pulses. In addition, because the broadband beam is over 3000 wavenumbers in bandwidth, when this beam is scattered by the unknown gas to produce a coherent Raman beam, the coherent Raman beam will also be over 3000 wavenumbers in bandwidth, thereby producing the entire gas phase vibrational Raman spectrum of the unknown gas without any gaps, which permits accurate identification of the gas.

The sample-filled Raman cell 38 is composed of a piece of copper tubing, attached at one end to the output of the gas chromatograph 40, and a T-shaped, hollow brass joint, whose bottom end (the bottom of the "T") is attached to the other end of the copper tubing. The copper tubing and T-shaped brass joint are wrapped in heating tape. The two sides at the top of the "T" are open at each end to permit light to freely enter and exit therefrom. The cell has no windows and is heated to prevent condensation of the sample gases as they emerge from the gas chromatograph 40.

Optically and Electrically Processing the Coherent Raman Beam from the Sample

Figure 4A:
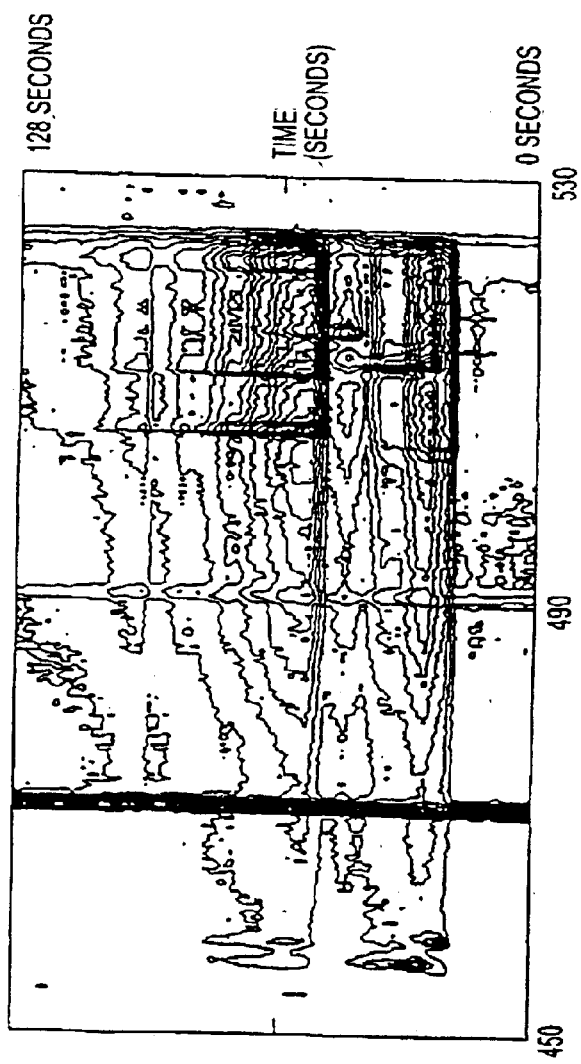
FIG. 4A shows a contour plot of the data from a monochromator measuring the time-lapse sequence of Raman spectra of various gasses after they are separated by a gas chromatograph.

The overlapping beams, called the input beams, interact with the flowing gases in the sample-filled Raman cell 38 to generate a coherent Raman beam. The coherent Raman beam, called the output beam, exits from one side of the "T" opposite from where the overlapping beams entered the "T". The output coherent Raman beam, which is mixed with the input, overlapping beams, is then reshaped and collimated by an 8 inch focal-length, plano-convex lens 42 (manufactured by Edmund Scientific, model no. 45,152), and enters optical filters 44 and 46 (manufactured by Schott Glass Technologies nos. KG3 and BG40, respectively), which absorb near infra-red light to remove one of the input beams. The remaining 532 nm input beam and the coherent Raman beam strike a holographic notch filter 47 (manufactured by Kaiser Optical Systems, model no. HNF-532.0-1.0), which removes the 532 nm beam by reflection. In the case of the alternative embodiment of FIG. 1 where the 532 nm beam is replaced by a narrowband coherent beam from a second OPO, filter 47 is replaced by a holographic notch filter made for the wavelength of the beam from the second OPO (such as model no. HNF-633-1.0 or HNF-488-1.0 manufactured by Kaiser Optical systems). The remaining output beam is then focused by an 8 inch focal-length, plano-convex lens 48 (manufactured by Edmund Scientific, model no. 45,152) into a 1.25 m monochromator 50 (manufactured by SPEX, model 1250 m) that is equipped with a 150 g/mm grating and a charge-coupled device (CCD) 51. The CCD 51 records spectra at a rate of 10 Hz (the repetition rate of the laser 12). The CCD 51 is attached to a computer (not shown) running software to analyze and display the data produced by the CCD 51. The computer stores the Raman spectra of the unknown gas and because the Raman spectrum covers a region of more than 3000 wavenumbers, the resulting spectra can be used to identify the gas from its Raman spectrum with high accuracy, as will be discussed in further detail below in conjunction with FIGS. 4A, 4B, and 4C. The computer may also average or accumulate the spectra produced by the CCD over longer time periods to improve signal-to-noise ratios and reduce the number of data files. The computer may, in addition, permit the data to be viewed as a sequence of spectra on a cathode ray tube or on a printed graph, as shown in FIG. 4A, or in matrix form (intensity as a function of time and wavelength).

Second Preferred Embodiment

Figure 3:
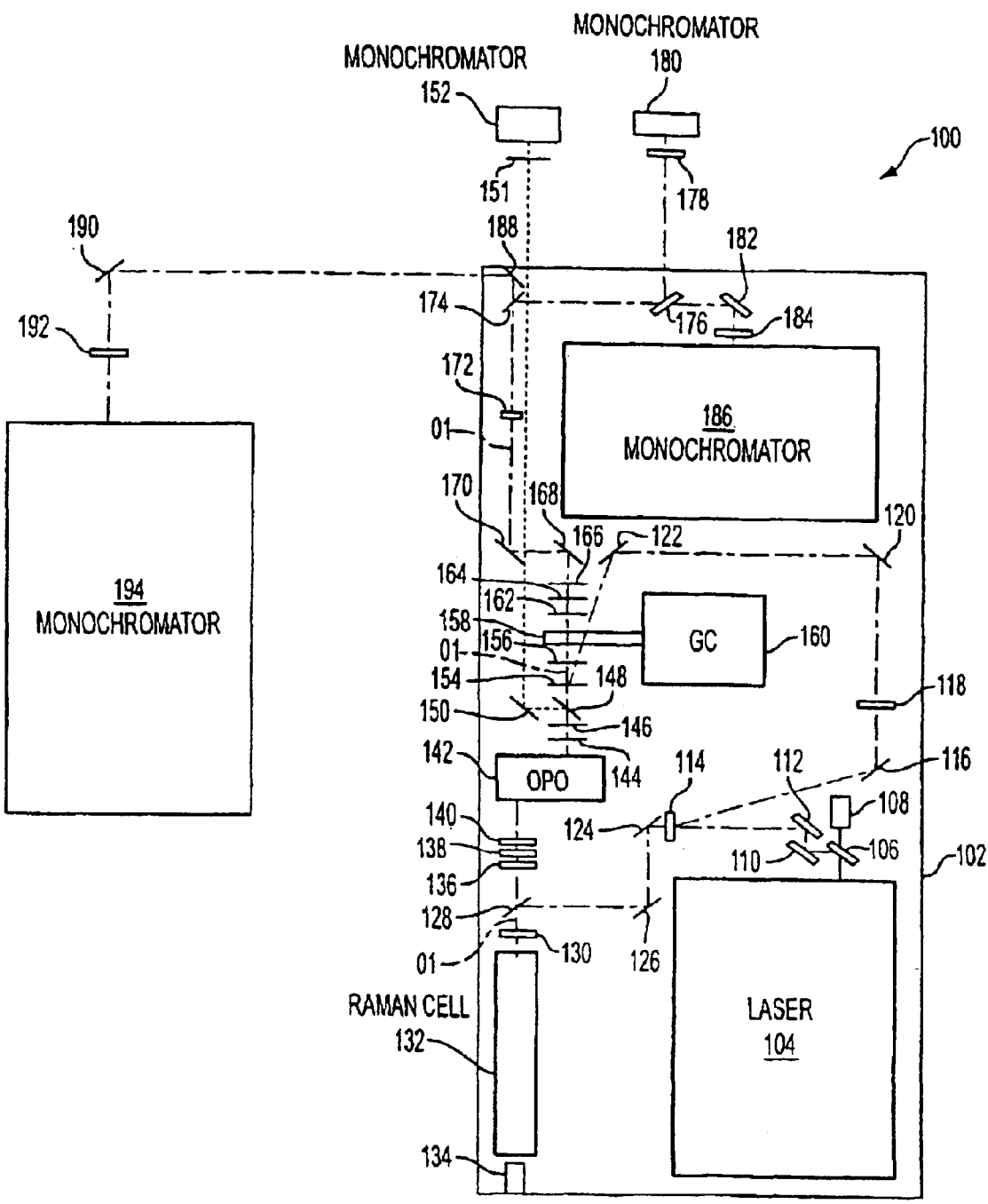
FIG. 3 is a schematic view of a second embodiment of the Multiplex Coherent Raman Radiation Detector.

FIG. 3 shows a second preferred embodiment of the multiplex coherent Raman detector 100. The laser, the OPO, the hydrogen-filled Raman cell, the sample-filled Raman cell, and the gas chromatograph are the same in the two embodiments, as are a number of the optical elements, as will be described below.

Introduction

The detector 100 detects the Raman radiation scattered from an unknown gas and uses that Raman radiation to determine the identity of the gas with higher accuracy than has been possible before. This advantageous effect occurs because the FIG. 3 embodiment also illuminates the unknown gas simultaneously with a broadband laser beam having a bandwidth of more than 3000 wavenumbers and a narrowband laser beam having a bandwidth of approximately 0.003 wavenumbers. This broadband and narrowband radiation, when scattered by an unknown gas, produces the entire gas phase vibrational Raman spectrum with a spectral resolution of approximately 0.003 wavenumbers without gaps and with a high signal-to-noise ratio, which permits an accurate identification of the gas. The narrowband laser beam is produced by an injection-seeded, near transform-limited Nd:YAG laser 12, which produces a laser beam having a bandwidth of 0.003 wavenumbers due to its being injection seeded. This broadband illumination is produced by an optical parametric oscillator. The optical parametric oscillator must be pumped by a sufficiently strong 683 nm beam to generate stable broadband radiation of sufficient intensity that the Raman radiation scattered by the unknown gas can be detected by a monochromator and a CCD. This task is accomplished by slightly tilting a hydrogen-filled Raman cell with respect to an incident 532 nm laser beam and optical axis. Such tilting increases the intensity of the 683 nm laser beam produced by the Raman cell to the required degree.

Production of Broadband and Narrowband Light for Sample Illumination Producing and Splitting of Laser Beam The detector 100 comprises a 3 foot by 12 foot optical table 102 supporting the components of the detector 100. The detector 100 further comprises an injection seeded Nd:YAG laser 104 that produces a second harmonic beam whose wavelength is 532 nm. The laser 104 has a 10 Hz repetition rate and the second harmonic beam produced thereby has an energy of about 200 mJ per 5 ns pulse. The second harmonic 532 nm beam is projected by the laser 104 to a dichroic mirror 106 that reflects 532 nm light and transmits 1064 nm light. 1064 nm light from the laser 104, which is not used in the detector 100, is transmitted through the dichroic mirror 106 to a beam dump 108. 532 nm light from the laser 104 is reflected by the mirror 106 to a dichroic mirror 110, which reflects the 532 nm beam to a dichroic mirror 112. Mirror 110 is identical to mirror 106. Mirror 112 reflects the 532 nm beam to a wedged window 114.

Splitting of the Laser Beam and Optically Delaying One of the Split Beams

The wedged window 114 reflects a portion of the 532 nm beam (approximately 5 mJ) to a variety of optical elements that delay its arrival at a gas chromatograph (identical to the gas chromatograph 40 used in the FIG. 1 embodiment). More specifically, the wedged window 114 reflects a portion of the 532 nm beam to a Pellin Broca prism 116, which reflects and refracts the beam through an iris diaphragm 118 to a broadband dielectric mirror 120. Prism 116 directs 532 nm light toward the diaphragm 118 and separates this 532 nm light from other wavelengths by refracting other wavelengths at a different angle than the 532 nm light. Therefore, diaphragm 118 spatially prevents wavelengths of light that are other than 532 nm from passing therethrough. The mirror 120 reflects the 532 nm beam to a silver coated mirror 122, which, in turn, reflects the 532 nm beam to a dichroic mirror, to be discussed later, that reflects the 532 nm beam, while transmitting a broadband 1100–1700 nm beam therethrough, thereby combining the beams for multiplex illumination of an unknown sample gas separated in the gas chromatograph, as will also be discussed later.

Transmitting of Other Split Laser Beam to Raman Cell

The remainder of the 532 nm beam that has not been reflected by the wedged window 114 passes through the wedged window and is reflected by a dichroic mirror 124. The dichroic mirror 124 reflects the 532 nm beam to a dichroic mirror 126, which in turn, reflects the 532 nm beam to a dichroic mirror 128. The dichroic mirror 128 reflects 532 nm light, while transmitting 683 nm light. As a result, the dichroic mirror 128 reflects the 532 nm beam along optical axis 01 to a 0.5 m focal-length plano-convex lens 130 that focuses the beam along optical axis 01 into a stainless steel Raman cell 132 filled with hydrogen. In response to receiving the focused 532 nm beam, the hydrogen-filled Raman cell 132 produces a backward-propagating, phase-conjugate, stimulated Raman-scattered 683 nm beam traveling back along the optical axis 01 toward the lens 130. The hydrogen-filled Raman cell 132 also produces radiation of other wavelengths, which is collected in a beam dump 134.

Producing a Broadband-light-production Driving Beam with a Raman Cell

The hydrogen-filled Raman cell 132 is one meter in length and is tilted approximately one degree with respect to the optical axis 01, the axis along which the input 532 nm beam travels. Applicants have discovered that the tilting of the hydrogen-filled Raman cell 132 increases the energy of the coherent Raman radiation it produces by as much as four times as compared to the energy of the coherent Raman radiation produced by the hydrogen-filled Raman cell 132 without tilting. Thus, in this embodiment, the energy of the 683 nm beam produced by the hydrogen-filled Raman cell 132 can reach 130 mJ when the incident 532 nm beam is 340 mJ. More typically, the laser 104 produces a 532 nm beam whose energy when entering the hydrogen-filled Raman cell 132 is approximately 200 mJ, thereby producing a 683 nm beam of 70 mJ. This increased energy of the coherent Raman radiation produced by the hydrogen-filled Raman cell 132 is needed to generate a sufficiently strong and stable broadband beam in the optical parametric oscillator (to be discussed below) that the Raman radiation produced in response to illuminating an unknown gas with the broadband beam has sufficient strength to be detected with a high signal-to-noise ratio without any gaps when using a monochromator, a CCD and a computer to determine the identity of the unknown sample gas. Without tilting, saturation of the Raman-scattering process within the hydrogen-filled Raman cell 132 limits the energy of the 683 nm pulse to about 30 mJ. In fact, at high 532 nm beam energies, saturation can cause the 683 nm beam energy to slightly decrease as the 532 nm beam energy is increased.

In addition, the effect of tilting was studied by focusing a beam of light from a tunable OPO into the Raman cell. The energy of the focused beam from the OPO remained a constant value of 52 mJ over the wavelength range of 531.7 nm to 532.3 nm. When not tilted, the backward-propagating stimulated Raman-scattered beam generated by the Raman cell was measured to be 13+/−2 mJ. After tilting, the backward-propagating beam energy increased to 18+/−2 mJ over the same wavelength range. The size of the increase was limited by the fact that the energy from the tunable OPO was small compared to that of Nd:YAG laser 104. The fact that the increase was observed over a range of wavelengths suggests that the effect responsible for the increase is insensitive to wavelength.

Figure 5:
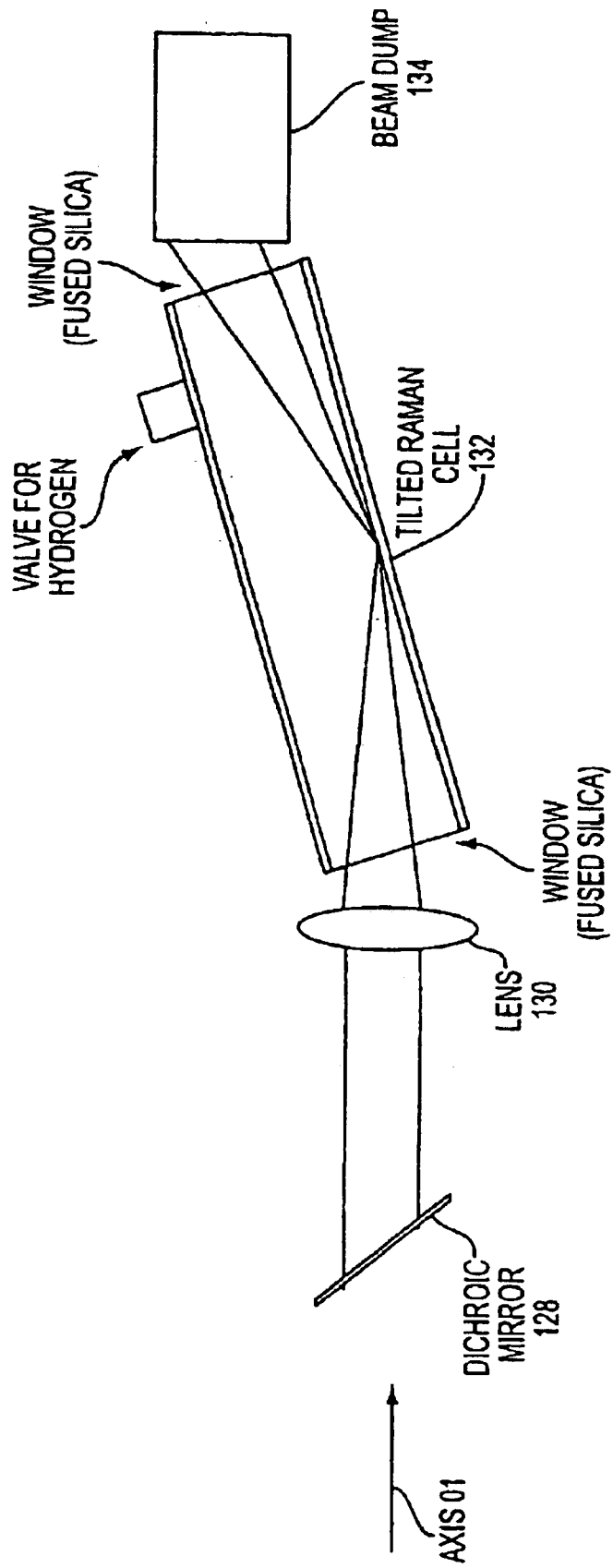
FIG. 5 is a schematic view of the hydrogen-filled Raman cell 20 shown in FIG. 1 and the tilting of the cell 20 with respect to the input beam.

FIG. 5 shows the tilting of the hydrogen-filled Raman cell 132 with respect to the optical axis 01 and the input beam, focused by the lens 130 on an inside side wall of the cell 132, after passing through the window of fused silica on the front face of the cell 132. The cell 132 is tilted, for maximum 683 nm beam energy, up to the angle at which less than the entire input beam enters a hole in the hydrogen-filled Raman cell, so that the focal point of the entire input beam in the hydrogen-filled Raman cell 132 collides with a side wall on the inside of the hydrogen-filled Raman cell. The structure of the cell 132 in FIG. 5 is identical to the cell 20 shown in FIG. 1 and cell 20 is tilted in an identical manner to the tiling of cell 132 in FIGS. 3 and 5.

As in the first embodiment, the quality of the 683 nm phase-conjugate beam produced by the Raman cell 132 is high and is almost identical to that of the 532 nm beam, which is high due to the Gaussian optics used in the Nd:YAG laser 104. In addition, the length of the backward-propagating pulse of the 683 nm beam produced by the Raman cell 132 is much shorter than the pulse of the incident 532 nm beam. But this disadvantage is overcome, as in the first embodiment, by creating a pulse train, using gas under high pressure in the Raman cell 132, such as at least 200 psi and preferably 400 psi of hydrogen, and by using an optical parametric oscillator of short cavity length of 5 inches or less, as will be discussed below.

The Raman cell 132 projects the 683 nm phase conjugate beam along the optical axis 01 through the lens 130, which collimates the beam and directs it through the dichroic mirror 128 to a telescope comprising a +175 mm focal-length, a plano-convex lens 136 and a −100 mm focal-length, plano-concave lens 138, which together reduce the diameter of the 683 nm beam. The reduced-diameter 683 nm beam then travels along the optical axis 01 to a half-wave plate 140, which rotates the beam polarization to a vertical polarization before it enters a free-running optical parametric oscillator (OPO) 142.

Producing Broadband Illumination with an Optical Parametric Oscillator

In response to receiving the 683 nm vertically-polarized beam, the OPO 142 produces a broadband beam of 1100–1700 nm covering a range of over 3000 wavenumbers, and more specifically 3200 wavenumbers. Using a beam with this broad a bandwidth (in combination with a narrow-band beam, as will be discussed below) permits the entire gas phase vibrational Raman spectrum of an unknown sample to be obtained, thereby permitting accurate identification of the sample. The OPO 142 is the same as the OPO 28 shown in FIGS. 1 and 2. Therefore, no further discussion of this element is provided.

The OPO 142 outputs a 1100 nm–1700 nm broadband beam at 5–10 mJ per pulse of the laser 104.

Calibrating the OPO Before Sample Illumination

The 1100 nm–1700 nm broadband beam emerging from the window of the OPO 142 enters a filter 144, which removes out any visible ambient light by absorption. The 1100 nm–1700 nm broadband beam then enters a 0.5 m focal-length piano-convex lens 146, which collimates the broadband beam. The collimated broadband beam then strikes a removable right angle turning prism 148. The prism 148 is placed on optical axis 01 before measurement of the Raman spectrum of a sample from a gas chromatograph for the purpose of determining the spectrum of the broadband beam generated by the OPO 142, as will be discussed below. The prism 148 is removed after such measurement and before the measurement of the Raman spectrum of the sample from the gas chromatograph. When the prism 148 is positioned at the position on the optical axis 01 shown in FIG. 3, the 1100–1700 nm beam from the OPO 142 is reflected to an identical right angle turning prism 150. The prism 150 reflects the beam through a 0.75 m focal-length, plano-convex lens 151 to the entrance of a 0.125 m scanning monochromator 152 with a pyroelectric detector, such as a Molectron Joulemeter (model J9LP). The signal from the pyroelectric detector is transmitted to a preamplifier (not shown) and then to a gated boxcar integrator (not shown), such as a Stanford Research Systems boxcar integrator, which captures the signal electronically so that it can be recorded. The resulting signal is recorded using a computer (not shown), equipped, for example with a data acquisition system and Labview software from National Instruments, which permits the spectrum of the OPO 142 to be determined before Raman-spectrum measurement of the unknown gas sample generated by the gas chromatograph.

Combining of Broadband and Narrowband Beams for Sample Illumination

When the prism 148 is removed from the optical axis 01, the 1100–1700 nm beam from the lens 146 strikes the dichroic mirror 154, which transmits the 1100–1700 nm broadband beam therethrough (it is capable of transmitting light from 1000 nm to 2000 nm therethrough). In addition, the dichroic mirror 154 receives the 532 nm beam from the mirror 122. The 532 nm beam has been delayed by wedged window 114, the Pellin Broca prism 116, the broadband dielectric mirror 120, and the mirror 122 so as to arrive at the dichroic mirror 154 at the same time as the 1100 nm–1700 nm broadband beam from lens 146. The dichroic mirror 154 reflects the delayed 532 nm beam along the optical axis 01 at the same time that the 1100 nm–1700 nm broadband beam passes through the dichroic mirror 154 and also travels along optical axis 01. As a result, the 532 nm beam and the 1100 nm–1700 nm broadband beam are spatially and temporally overlapped as they travel from the dichroic mirror 154 along optical axis 01. Alternatively, a separate laser or laser-like source (not shown) may be used as the source of the 532 nm beam. If this alternative source generates a wavelength other than 532 nm, then a different dichroic mirror that reflects this new wavelength may be used. An example of an alternative source is an OPO such as a Spectraphysics MOPO 730 with a frequency doubler, which can generate light over the range of 220 nm to 1800 nm.

Illuminating an Unknown Sample with Narrowband and Broadband Light

The two overlapping beams then pass through an 8 inch focal-length, plano-convex lens 156, which focuses the two overlapping beams to a point on optical axis 01 in a heated, sample-filled Raman cell 158 that receives a stream of gases (i.e., the unknown sample whose identity is to be determined by detector 100) from a gas chromatograph 160. The two overlapping beams interact with the unknown gas to produce coherent Raman radiation, whose spectrum can be analyzed to determine the gas's identity, as will be discussed below. Lens 146 ensures that the lens 156 focuses the two overlapping beams at the same point on optical axis 01. This use of overlapping narrowband and broadband beams to illuminate a sample to produce spectrally broad coherent Raman radiation is known as multiplex coherent Raman scattering and is necessary to produce coherent Raman spectra rapidly (at 10 Hz, the repetition rate of laser 104). In addition, because the broadband beam is over 3000 wavenumbers in bandwidth, when this beam is scattered by the unknown gas to produce a coherent Raman beam, the coherent Raman beam will also be over 3000 wavenumbers in bandwidth, thereby producing the entire gas phase vibrational Raman spectrum of the unknown gas without gaps, which permits accurate identification of the gas. The sample-filled Raman cell 158 is the same as the sample-filled Raman cell 38 in the FIG. 1 embodiment.

The overlapping beams, called the input beams, enter one of the two sides at the top of the "T" and interact with the flowing gases in the sample-filled Raman cell 158 to generate a coherent Raman beam. The coherent Raman beam, called the output beam, exits from the other of the two sides at the top of the "T" along with the input, overlapping beams. The output, coherent Raman beam, which is mixed with the input, overlapping beams, is then reshaped and collimated by an 8 inch focal-length, plano-convex lens 162 and enters optical filters 164 and 166, which absorb near infra-red light to remove one of the input beams. The remaining 532 nm input beam and the coherent Raman output beam then strike a silver coated mirror 168, which reflects these beams to a broadband dielectric mirror 170. The mirror 170 reflects these beams through a holographic notch filter 172, which removes the 532 nm input beam by reflection.

Adjusting the Detector 100 to Maximize the Coherent Raman Beam

A removable silver coated mirror 174 is positioned in the optical path 01 of the filtered output beam, filtered by the filters 164, 166, and 172, before identification of the sample in the sample-filled Raman cell 158 for the purpose of adjusting the optics in the detector 100 to maximize the intensity of the Raman radiation scattered from the sample gas in the sample-filled Raman cell 158. To accomplish this goal, the mirror 174 is inserted into the optical path 01 and light from laser 104 is projected through the optics of the detector 100 to the sample-filled Raman cell 158 when the sample-filled Raman cell 158 has only ambient air therein. Coherent Raman radiation generated from the ambient air and filtered by the filters 164, 166, and 172 is reflected by the mirror 174 to a removable silver coated mirror 176, which reflects the filtered output beam through a 2 inch focal-length, plano-convex lens 178, which focuses the filtered output beam into a 0.125 m double monochromator 180 with an R928 photomultiplier tube (PMT). The PMT measures the intensity of the coherent Raman signal so that the optics of the detector 100 can be adjusted before sample identification to maximize the intensity of the coherent Raman signal. This is accomplished by setting the monochromator 180 to a wavelength of a species that is present in ambient air, such as nitrogen, which is 473 nm. The signal is then viewed on an oscilloscope and the optics that direct the 532 nm beam and the OPO beam into the sample-filled Raman cell 158 are adjusted to maximize the signal detected by the PMT.

Processing of Coherent Raman Radiation

Once the intensity of the coherent Raman radiation has been optimized, either 1) the mirror 176 is removed from the optical path of the filtered output beam reflected by the mirror 174, so that the filtered output beam reflected by mirror 174 strikes a silver coated mirror 182, which reflects the filtered output beam through a 50 mm focal-length, plano-convex lens 184, which focuses the filtered output beam into a 0.25 m monochromator 186 with an Andor Technology iCCD (not shown), or 2) the mirror 174 is removed from the optical path 01, so that the filtered output beam having passed through filter 172 is reflected by a broadband dielectric mirror 188 to a silver coated mirror 190, which reflects the filtered output beam through an 8 inch focal-length plano-convex lens 192, which focuses the filtered output beam onto a 1.25 m monochromator 194 with a CCD (not shown).

The CCD and the iCCD are connected to computers (not shown) running SpectraMax for Windows software or Intraspec software to control the monochromators, and to acquire data from the CCD and the iCCD and to display and analyze the results. The computer records and analyzes the Raman spectrum of the unknown gas and because the Raman spectrum has more than 3000 wavenumbers, the spectrum can be used to identify the gas from its Raman spectrum with high accuracy, as will be discussed in further detail below in conjunction with FIGS. 4A, 4B, and 4C. For species with similar spectra, the ability to distinguish between them often depends upon the resolution of the instrument. For additional accuracy in identifying such species, the monochromators may be operated in a high resolution mode by using high density gratings (1200 g/mm or 2400 g/mm). Other ways to improve the resolution include decreasing the size of the pixels on the CCD and increasing the focal length of the monochromator. For example, monochromator 194 has a focal length of 1.25 meters, a CCD pixel size of 27 microns, and can be equipped with a 1200 g/mm grating. The resulting pixel-to-pixel resolution is 0.7 wavenumbers (in units of $cm^{-1}$), which is considerably better than the resolution commonly found in infrared detectors for gas chromatography (4 or 8 wavenumbers). The computer may also average or accumulate the spectra produced by the CCD over longer time periods to improve signal-to-noise ratios and reduce the number of data files. The computer may, in addition, permit the data to be viewed as a sequence of spectra on a cathode ray tube or on a printed graph, as shown in FIG. 4A, or in matrix form (intensity as a function of time and wavelength).

The FIG. 3 embodiment can identify a sample of mass of at least 100 micrograms. But it is within the scope of the present invention to modify the FIG. 3 embodiment to reduce this number by a factor of 104 by reducing the size of the sample-filled Raman cell 158 to have an hourglass shape (with its smallest diameter being of the order of tens of microns) to match the shape of the overlapping beams when they are focused inside the sample-filled Raman cell 158. It is also within the scope of the present invention to further reduce the detection limits of the mass of the sample by a factor of $10-10^6$ by using resonance enhancement by varying the wavelength of the 532 nm beam to match the electronic level of the sample molecule. The limit on the mass of the sample that can be identified is determined ultimately by the level of noise in the nonresonant background, which is a nonzero broad background that is normally found in coherent (nonlinear) spectroscopy.

Below in Table 1 are listed the manufacturers and model numbers of many of the elements of the FIG. 3 embodiment.

TABLE 1

| Element | Manufacturer | Model Number |
|---|---|---|
| 102 | Newport | RS 3000 |
| 104 | Spectraphysics | GCR-230 with EEO-355 option |
| 106 | CVI | BSR-51-1025 |
| 108 | Spectraphysics | BD5 |
| 110 | CVI | BSR-51-1025 |
| 112 | CVI | Y2-1025-45-UNP |
| 116 | CVI | PLBC-10.0-79.5C |
| 118 | Thorlabs | ID25 |
| 120 | Thorlabs | BB1-r1 |
| 122 | Newfocus | 5103 |
| 124 | CVI | Y2-1025-45-UNP |
| 126 | CVI | Y2-1025-45-UNP |
| 128 | CVI | Y2-1025-45-UNP |
| 130 | Coherent | 43-0546-000 |
| 132 | Taitech | 1 meter stainless steel cell |
| 134 | Thorlabs | BT510 |
| 136 | Edmund Scientific | 32,866 |
| 138 | Edmund Scientific | 45,027 |
| 140 | LaserVision | no model number |
| 142 | LaserVision | Custom-built, see FIG. 2 |
| 144 | Schott Glass Technologies | RG830 |
| 146 | Coherent | 43-0546-000 |
| 148 | Coherent | 24-8096-000 |
| 150 | Coherent | 24-8096-000 |
| 151 | Coherent | 43-0553-000 |
| 152 | CVI | cm110 |
| 154 | CVI | LWP-0-RUNP532-TUNP1000-2000 |
| 156 | Edmund Scientific | 45,152 |
| 160 | Gow Mac | 400 |
| 162 | Edmund Scientific | 45,152 |
| 164 | Schott Glass Technologies | KG3 |
| 166 | Schott Glass Technologies | BG40 |
| 168 | Newfocus | 5103 |
| 170 | Thorlabs | BB1-r1 |
| 172 | Kaiser Optical Systems | HNF-532.0-1.0 |
| 174 | Newfocus | 5103 |
| 176 | Newfocus | 5103 |
| 178 | Edmund Scientific | 32,971 |
| 180 | CVI | cm112 |
| 182 | Newfocus | 5103 |
| 184 | Edmund Scientific | 32,971 |
| 186 | Oriel | MS257 |
| 188 | Thorlabs | BB1-r1 |
| 190 | Newfocus | 5103 |
| 192 | Edmund Scientific | 45,152 |
| 194 | Spex | 1250 m |

Table 2, shown below, lists the preferred values and preferred ranges of some of the elements in the embodiments shown in FIGS. 1 and 3.

TABLE 2

| Item | Value | Range |
|---|---|---|
| Hydrogen Pressure in Raman cell used to produce 683 nm beam | 400 psi | >200 psi |
| Pump wavelength for Raman cell used to produce 683 nm beam | 532 nm | 500–550 nm |
| Tilt angle of Raman cell | 1.0 degrees | >0 but <2.2 degrees, so that beam focuses onto side of Raman cell. |
| 532 nm pump energy input into Raman cell producing 683 nm beam | 200 mJ in a 5–8 ns pulse | 50–400 mJ |
| Wavelength to pump OPO | 683 nm | 650–700 nm |
| BBO crystal | Type I BBO, 5 mm × 5 mm × 14 mm (long), two opposite small faces coated with a single layer of magnesium fluoride, centered at 700 nm (broadband), cut at 22 ± 0.5 degrees. | |
| Length of oscillator cavity of OPO | 5 inches | 1–10 inches |
| Length of Raman cell producing 683 nm beam | 1 meter | 0.1–2 meters |
| Telescope lenses | Focal lengths of +175 mm and −100 mm | Any combination that reduces the beams to match the aperture of the BBO crystals (5 mm × 5 mm). |
| Repetition rate of laser | 10 Hz | Any rate that is sufficiently high to take spectra rapidly (e.g., >1 Hz). |
| Carrier gas for gas chromatograp | Nitrogen | Any carrier gas that can be used for gas chromatography |

Timing of Various Operations

In both preferred embodiments described above, the unknown sample is injected into the gas chromatograph at the same time that data acquisition is started by projecting a laser pulse out of the laser and recording data with the computer. The light-producing components of the detectors 10 and 100 are preferably turned on 30–45 minutes in advance of the injection (e.g. the laser, the hydrogen-filled Raman cell producing the 683 nm beam, and the. OPO) to ensure stability of the components, and are usually left running before and between movement of gas from the gas chromatographs 40 and 160 into the sample-filled Raman cells 38 and 158. The gas chromatographs 40 and 160 are preferably turned on several hours before the injection of the sample and movement of the gaseous sample from the gas chromatographs 40 and 160 into the sample-filled Raman cells 38 and 158 to ensure temperature stability. In addition, carrier gases which carry the sample placed in the gas chromatograph can include nitrogen (which provides a single sharp peak at 472 nm), or helium, which has no vibrational Raman signal because it is an atom, not a molecule, and only molecules produce vibrational Raman spectra. The peak from the nitrogen can be used as a method to calibrate the detectors 10 and 100, as has been previously discussed.

Experimental Results

The FIG. 3 embodiment has been used to detect and identify the components of mixtures after they have been separated using gas chromatography. A mixture containing benzene, acetone, methanol, carbon tetrachloride, chloroform, and cyclohexane, was separated with gas chromatography, and the individual components were identified spectroscopically, even when chromatographic peaks were overlapped, as will now be discussed.

FIG. 4A shows a two-dimensional reduction of a three-dimensional contour plot generated by a computer from data produced by a CCD connected to monochromator 194 with a 150 g/mm grating measuring the coherent Raman radiation scattered from a gas mixture containing the six compounds that was injected in the gas chromatograph 160. The X axis represents wavelength in nanometers, ranging from 450 nm to 530 nm, while the Y axis represents time, ranging from 0 seconds to 128 seconds. The Z axis (not shown) of the three-dimensional contour plot represents the intensity of the detected light. Intensity is depicted in the two-dimensional graph shown in FIG. 4A by the spacing between contour lines, i.e., the closer the lines, the greater the change in signal at a particular time and wavelength. Signals that are more intense cause a greater change in the contour plot and appear as darker regions of more closely spaced lines. Over a period of 128 seconds, different gases, that have been separated in time by the gas chromatograph 160 will enter the sample-filled Raman cell 158 for measurement. Therefore, over time, the detector 100 will detect coherent Raman radiation from different compounds. And since these different compounds produce (when illuminated with the overlapping narrowband and broadband light) coherent Raman radiation having different spectra from each other, the coherent Raman spectra shown in FIG. 4A will change over the course of 128 seconds, which is what is seen in FIG. 4A.

Figure 4B:
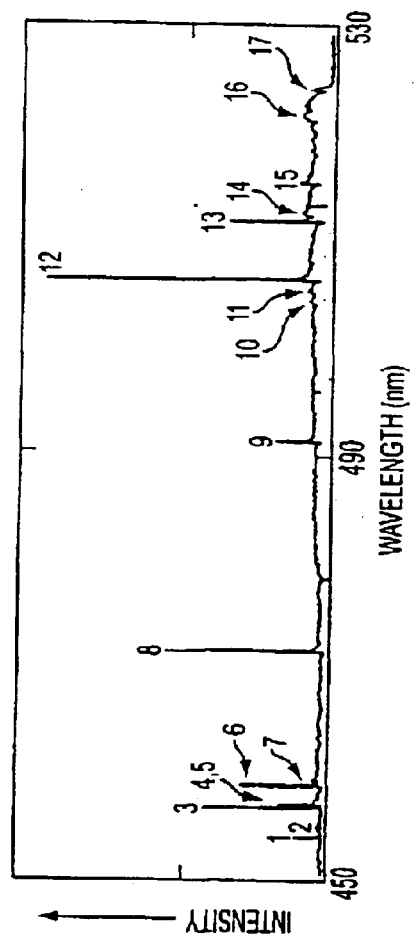
FIG. 4B shows a graph of data from a monochromator measuring the Raman spectrum of the same gasses as in FIG. 4A, but before they are separated by the gas chromatography.

FIG. 4B is a graph of data generated using the same gas species and the same equipment used in FIG. 4A, except that a 1200 g/mm grating was used in conjunction with the monochromator 194, and except that measurements of the Raman spectrum of the mixture were taken while the gas mixture was held stationary in a separate room-temperature cell before the gases of the mixture were separated by the gas chromatograph. Moreover, unlike FIG. 4A, the Y axis represents the intensity of the Raman radiation detected by the CCD and the computer. FIG. 4B contains seventeen numbers, nos. 1–17, each of which designate a different peak on the graph. Each peak is associated with a specific compound, because different compounds have characteristic peaks on such a graph of their Raman spectrum. Moreover, different compounds will shift the wavelength and wavenumbers of light projected thereon by a characteristic and known amount when they scatter such light. Therefore, from the-various peaks on such a graph, the identity of the compounds in the mixture can be determined. Accordingly, Table 3 below lists the identity of each compound, called a species, the wavelength at which its characteristic peak exists, and the shift in wavenumbers produced when the compound scatters light to produce coherent Raman radiation.

TABLE 3

| Peak | Species | Wavelength | Shift in wavenumbers (cm$^{-1}$) |
| --- | --- | --- | --- |
| 1 | Benzene | 457.3 | 3073 |
| 2 | Chloroform | 458.2 | 3030 |
| 3 | Cyclohexane | 459.9 | 2950 |
| 4 | Acetone | 460.2 | 2936 |
| 5 | Cyclohexane | 460.2 | 2936 |
| 6 | Cyclohexane | 461.8 | 2860 |
| 7 | Methanol | 462.2 | 2841 |
| 8 | Nitrogen | 473.2 | 2339 |
| 9 | Oxygen | 491.4 | 1556 |
| 10 | Methanol | 503.6 | 1063 |
| 11 | Methanol | 504.5 | 1027 |
| 12 | Benzene | 505.4 | 992 |
| 13 | Cyclohexane | 510.3 | 802 |
| 14 | Acetone | 511.5 | 756 |
| 15 | Chloroform | 513.7 | 672 |
| 16 | Carbon tetrachloride | 519.5 | 455 |
| 17 | Chloroform | 522.1 | 359 |

The identity of species in FIG. 4A can be determined by finding the X axis position of the event (or peak, characterized by a dark region of closely spaced lines) and comparing it to a list of positions for various compounds such as are listed in Table 3. If a compound from Table 3 is present at any time during a measurement, there will be an event at the corresponding X axis positions. Tables of compounds that are very large are referred to as "libraries," and can be used as a reference for identifying unknown compounds. When used with these libraries, computers can be used to match spectra from unknown compounds with known compounds and identify the unknown compounds automatically. For example, nitrogen (peak #8 in FIG. 4B) is the carrier gas that carries the six-compound mixture in the gas chromatograph, and is present at all times during the separation in the gas chromatograph. This fact is confirmed by the presence of a dark solid vertical line on the graph in FIG. 4A directly above peak #8 in FIG. 4B. Moreover, the portion of the graph in FIG. 4A above peak #1 (representing benzene) in FIG. 4B appears slightly before the midpoint (in time) of the experiment, indicating that benzene appears at this point in time. In addition, peak #12 in FIG. 4B also represents benzene, and appears at the same point in time as peak #1. The portion of the graph in FIG. 4A for cyclohexane above peaks #3, #5, #6, and #13 in FIG. 4B appear around the same time as those for benzene. Benzene and cyclohexane are therefore not resolved temporally by the gas chromatograph itself, but are resolved spectroscopically because the peaks appear at different wavelengths. On the other hand, peak #5 for cyclohexane is not spectroscopically resolved from peak #4 for acetone. However, acetone appears in FIG. 4A earlier (lower) than cyclohexane (acetone's features in FIG. 4A are above peaks #4 and #14 in FIG. 4B) and is therefore temporally resolved. Despite the fact that peaks #4 and #5 occur at the same wavelength, cyclohexane and acetone can be distinguished (by noting the arrival of features in FIG. 4A above peak #14 before features in FIG. 4A above peaks #3, #6, and #13) because the instrument's bandwidth is sufficient to cover the entire vibrational region. By using this procedure, all the compounds in the mixture injected into the gas chromatograph 160 can be determined with absolute certainty.

Figure 4C:
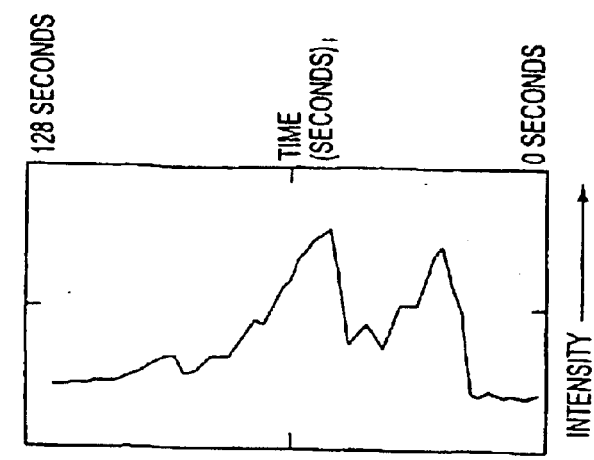
FIG. 4C shows a graph of the integrated signal from the monochromator (integrated over wavelength) as a function of time.

FIG. 4C shows a graph of the integrated signal (integrated over wavelength) from the CCD as a function of time. The Y axis is identical to that of FIG. 4A. However, the X axis is the integrated intensity of the signal produced by the CCD. This graph produces results analogous that which would be obtained using a gas chromatograph equipped with a simple non-selective detector (e.g., one that cannot provide spectra, and only uses retention time for identifying compounds).

Experimental Conditions

An 80 microliter mixture of 6 compounds (acetone, methanol, cyclohexane, carbon tetrachloride, chloroform, benzene) was injected into the gas chromatograph 160. The mixture contained equal parts of all the compounds except for benzene, which was present in an amount that was half the amount of the other compounds.

A Gow Mac 400 isothermal gas chromatograph was used. The carrier gas was nitrogen, flowing at 1.4 ml/sec. The column was 4'x¼" o.s. DC-200 on Chromasorb P WA DMCS, 80/100 mesh, at a temperature of 135 degrees C.

An SPEX 1250 m. (1.25 meter) monochromator with a 150 g/mm diffraction grating was used. The data acquisition software used was SPEX DM3000s, which is an old DOS-based program of limited resolution and data accumulation ability. Spectra were acquired every 2 seconds, with a slight delay (<0.5 seconds) between each spectrum. The contour plot was produced by combining 57 spectra. The total accumulation time was 2 minutes and 8 seconds.

The 532 nm beam had an energy of approximately 1 mJ/pulse, and the broadband beam energy generated by the OPO 142 was 4–5 mJ/pulse.

Alternate Embodiments and Alternate Variations

It is within the scope of the present invention to substitute for the monochromator and CCD, any spectroscopic device (monochromator or interferometer) capable of quickly analyzing the intensity of light as a function of wavelength, such as a Fourier Transform Interferometer, Hadamard transform spectrometer, Echelle spectrometer, and multiple stage monochromators.

It is also within the scope of the present invention to substitute for the gas chromatograph any separation instrument or technique (e.g., chromatography, electrophoresis, etc.) capable of separating a mixture into individual components, such as high pressure liquid chromatography, capillary electrophoresis, gel electrophoresis, ultracentrifuge, thin-layer chromatography, liquid chromatography, column chromatography, and paper chromatography.

It is also within the scope of the present invention to substitute for the Nd:YAG laser any other laser or laser-like device capable of illuminating (optically pumping) a Raman cell to produce a beam of light at or near 683 nm, such as a Ti: sapphire laser, an Excimer laser, a Dye laser, an OPO, and a Nd:YLF laser.

In addition, it is within the scope of the present invention to substitute for the hydrogen-filled Raman cell producing the 683 nm beam, any device capable of generating light from 600–800 nm with sufficient energy to illuminate (optically pump) an optical parametric oscillator, such as a Dye laser, a Ti: Sapphire laser, an Alexandrite laser, and a Ruby laser.

It is within the scope of the present invention to substitute for the OPO any device capable of generating broadband light covering a continuous range of >3000 wavenumbers, with sufficient energy and adequate beam properties to drive a coherent Raman process, such as other optical parametric devices, an optical Parametric amplifier, a white light generator, and a Ti: sapphire laser-based device.

It is also within the scope of the present invention to substitute for the narrowband 532 nm beam (that is overlapped with the broadband light) light at any other wavelength from any other laser or laser-like source, such as a tunable second optical parametric oscillator having a tuning range from 220 nm to 1800 nm and a bandwidth of 0.2 wavenumbers.

It is also within the scope of the present invention to substitute for the 10 Hz Nd:YAG laser and CCD detector any laser and detector with different repetition rates and acquisition speeds.

It is also within the scope of the present invention to substitute for the 532 nm beam from the Nd:YAG laser a beam at any wavelength from any laser or similar source of light to pump the Raman cell in such a way that tilting of the Raman cell causes an enhancement of the resulting Raman-shifted beam, such as a beam of light from an OPO that has a wavelength that can be varied from 220 nm to 1800 nm.

It is also within the scope of the present invention to substitute for the Nd:YAG, the hydrogen-filled Raman cell, and the OPO, any device or combination of devices capable of generating broadband light with sufficient energy and adequate beam properties to drive a coherent Raman process, such as dye lasers, diode lasers, diode-pumped lasers, white light generators, and Ti:Sapphire lasers.

It is further within the scope of the present invention to substitute for the monochromators, any spectroscopic device (monochromator or interferometer) capable of analyzing the intensity of light as a function of wavelength, such as a Fourier transformer, an infrared spectrometer, and a near infrared spectrometer.

It is also within the scope of the present invention to substitute for the mirrors used in detectors 10 and 100, any device capable of reflecting or partially reflecting or redirecting a beam of light, such as beam splitters, prisms, fiber optics, and diffraction gratings.

In addition, it is within the scope of the present invention to substitute for the right angle prisms, any device capable of reflecting or redirecting a beam of light, such as mirrors, fiber optics, and diffraction gratings.

It is also within the scope of the present invention to substitute for the Pellin Broca prism, any device capable of spectrally purifying a beam of light, such as diffraction gratings, other prisms, and other refractive optics.

It is also within the scope of the present invention to substitute for the dichroic mirrors, any device capable of reflecting a beam of light in a specific wavelength range, such as diffraction gratings, holographic optics, prisms, and fiber optics.

It is within the scope of the present invention to substitute for the lenses used in the detectors 10 and 100, any device capable of focusing, defocusing, collimating, or changing the diameter of a beam of light, such as prisms, curved mirrors, and Fresnel optics.

Moreover, it is within the scope of the present invention to substitute for the wedged window, any device capable of reflecting or extracting a portion of a laser beam, such as beam splitters, partially reflecting mirrors, anti-reflection coated optics, and surface of an optic such as a prism.

It is within the scope of the present invention to substitute for the filters, any device capable of absorbing, reflecting, or otherwise attenuating light, such as other filters, gases, liquids, dichroic mirrors, prisms, diffraction gratings, and beam splitters.

It is within the scope of the present invention to substitute for the iris diaphragm, any device capable of spatially selecting part of a beam of light, such as a pinhole, slit, or other aperture.

It is also within the scope of the present invention to substitute for the heated sample-filled Raman cells 38 and 158, any device capable of directing a stream of gas so that it follows a desired pathway and permits light to enter and exit, such as glass or quartz cells, cells made of other materials such as other metals, and cells made with different shapes or sizes that serve the same purpose.

It is also within the scope of the present invention to substitute for the computer and software, the oscilloscope, the preamplifier, and the boxcar integrator, any device capable of providing diagnostics, data acquisition, data analysis, and electronic control of instrumentation, such as chart recorders, other forms of software, and photon counters.

Further, it is within the scope of the present invention to substitute for the photomultiplier tube and pyroelectric detector, any device capable of detecting and measuring light intensity, such as phototubes, photo diodes, calorimeters, thermopiles, Si or Ge detectors, PbS or PbSe detectors, and other semiconductor detectors.

It is also within the scope of the present invention to substitute for the narrowband 532 nm beam, a beam of light at any wavelength that is generated by a laser-like device, such as laser or an OPO.

It is also within the scope of the present invention to use additional beams of light, in addition to a narrowband and a broadband beam, in order to generate the coherent Raman signal, such as beams of light from another laser, from an optical parametric device, from a Raman shifter, from a white light generator, and from a nonlinear optical device.

It is also within the scope of the present invention to use this detection system for applications other than to determine the identity of unknown gases separated by a gas chromatograph, such as applications requiring high spatial, temporal, and spectrographic resolution. Examples include combustion diagnostics, pump-probe spectroscopy, chemical vapor deposition diagnostics, laser ablation diagnostics, high resolution molecular spectroscopy, atomic spectroscopy, molecular dynamics, resonance Raman spectroscopy, electronic spectroscopy, microscopy, and other applications of gas phase spectroscopy.

It is also within the scope of the present invention to use this detection system or components of this system to study condensed phase samples (liquids and solids).

It is also within the scope of the present invention to substitute for the dual broadband CARS method, another method to produce a multiplex coherent Raman output capable of generating the entire vibrational spectrum, such as dual Stokes CARS, dual pump CARS, and dual pump-Stokes CARS.

It is also within the scope of the present invention to substitute for the CCD or iCCD any other device capable of simultaneously detecting the intensities of several portions of spatially separated light, such as diode array detectors, multichannel plate detectors, charge injected devices, and other array detectors.

It is also within the scope of the present invention to record spectra from regions outside of 450–530 nm. For example, the following other regions may be recorded: 534–600 nm for viewing a region called the Stokes region, 530–534 nm for viewing pure rotational peaks, and additional regions of the spectrum if the wavelength of the 532 nm beam is changed.

It is also within the scope of the present invention to substitute for the BBO crystals inside the OPO, any other material capable of generating light through a nonlinear effect, such as KDP, KTP, LiNbO$_3$, LiIO$_3$, and AgGaS$_2$.

It is also within the scope of the present invention to substitute for the OPO, any other device or method for generating a broadband beam, such as non-collinear phasematching, and pumping an OPO with a broadband source.

It is also within the scope of the present invention to substitute for the half-wave plate, any other device or method for altering the polarization of light, such as other types of wave plates, optics based on birefringent materials, and multiple-reflection devices.

It is also within the scope of the present invention to substitute for the diffraction gratings in the monochromators, any other diffraction gratings, such as diffraction gratings of different groove densities, such as those ranging from 1 g/mm to 10000 g/mm.

It is also within the scope of the present invention to substitute for the monochromators used in FIGS. 1 and 3, any other types of monochromators, such as monochromators of different focal lengths, such as those ranging from 0.06 m to 5 meters.

It is also within the scope of the present invention to substitute for the CCD and iCCD's used in FIGS. 1 and 3, any other type of CCD's, including those using different pixel sizes, such as those ranging from 1 micron to 100 microns in height and width or a different number or arrangement of pixels, covering a range from 2 pixels×2 pixels to 10000 pixels×10000 pixels. For example, a CCD with a pixel size of 13.5 microns would allow the monochromater 194 to have a pixel-to-pixel resolution of 0.4 wavenumbers.

It is also within the scope of the present invention to use other methods for combining the broadband and narrowband beams, such as noncollinear, two dimensional or three dimensional phasematching where an additional beam may be added or a beam may be separated into two beams in order to allow angles to be introduced between the beams.

What is claimed is:

1. An apparatus comprising:
    a narrowband coherent light source producing a narrowband coherent beam having a bandwidth of less than 1 wavenumber;
    a broadband coherent beam generator generating a broadband coherent beam having a bandwidth of more than 3000 wavenumbers; and
    an optical device configured and positioned to direct the narrowband coherent beam and the broadband coherent beam to a sample simultaneously to produce coherent Raman radiation scattered from the sample and comprising the complete vibrational Roman spectra of the sample with a spectral resolution of less than one wavenumber.

2. The apparatus defined by claim 1, wherein said broadband coherent beam generator generates a broadband coherent beam using the narrowband coherent beam as an input.

3. The apparatus defined by claim 1, wherein said narrowband coherent light source comprising an optical parametric oscillator.

4. The apparatus defined by claim 1, wherein said narrowband coherent light source comprises a lasers.

5. The apparatus defined by claim 1, wherein said narrowband coherent light source produces a narrowband laser hewn having a bandwidth of about 0.003 wavenumbers.

6. The apparatus defined by claim 1, wherein said broadband coherent beam generator generates a broadband coherent beam having wavelengths from about 1100 nm to about 1700 nm.

7. The apparatus defined by claim 1, further comprising:
    a gas chromatograph producing the sample in the form of one or more separated gaseous species; and
    a sample-filled Raman cell attached to said gas chromatograph for receiving the gaseous sample, wherein said optical device directs the broadband coherent beam and the narrowband coherent beam to said sample-filled Raman cell.

8. The apparatus defined by claim 1, wherein said narrowband coherent light source comprises an injection seeded, near transform-limited Nd:YAG laser.

9. The apparatus defined by claim 1, wherein said narrowband coherent light source comprises a Q-switched laser.

10. The apparatus defined by claim 1, further comprising:
    a driving device configured and positioned to produce a driving beam directed to said broadband coherent beam generator to cause the production of the broadband coherent beam from said broadband coherent beam generator; and
    wherein said optical device is positioned and configured to split said narrowband coherent beam into first and second narrowband coherent beams, to direct the first narrowband coherent beam to said driving device, and to direct the second narrowband coherent beam to the sample.

11. The apparatus defined by claim 10, wherein said driving device comprises a Raman cell filled with a gas and generating a backward-propagating, phase-conjugate beam of Raman radiation comprising the driving beam in response to receiving the first narrowband coherent beam.

12. The apparatus defined by claim 11, wherein said Raman cell is tilted with respect to an optical axis along which the first narrowband coherent beam travels toward said Raman cell.

13. The apparatus defined by claim 12, wherein said Raman cell is tilted about 1 degree with respect to the optical axis.

14. The apparatus defined by claim 12, wherein said Raman cell is tilted more than 0 degrees and less than 2.2 degrees with respect to the optical axis.

15. The apparatus defined by claim 1, wherein said broadband coherent beam generator comprises an optical parametric oscillator.

16. The apparatus defined by claim 15, wherein said optical parametric oscillator comprises two tiltable beta barium borate crystals that continuously emit broadband light in the range of 1100 to 1700 nm in response to receiving a driving pulse in the range of 10–130 mJ per pulse.

17. An apparatus comprising:
    means for producing a narrowband coherent beam having a bandwidth of less than 1 wavenumber;
    means for generating a broadband coherent beam having a bandwidth of more than 3000 wavenumbers; and
    means for directing the narrowband coherent beam and the broadband coherent beam to a sample simultaneously to produce coherent Raman radiation scattered from the sample and comprising the complete vibrational Raman spectra of the sample with a spectral resolution of less than one wavenumber.

18. The apparatus defined by claim 17, wherein said broadband coherent beam generating means generates a broadband coherent beam using the narrowband coherent beam as an input.

19. The apparatus defined by claim 17, wherein said narrowband coherent light source comprises an optical parametric oscillator.

20. The apparatus defined by claim 17, wherein said narrowband coherent light source comprises a laser.

21. The apparatus defined by claim 17, wherein said narrowband coherent beam producing means produces a narrowband coherent beam having a bandwidth at about 0.003 wavenumbers.

22. The apparatus defined by claim 17, wherein said broadband coherent beam generating means generates a broadband coherent beam having wavelengths from about 1100 nm to about 1700 nm.

23. The apparatus defined by claim 17, further comprising:
    means for performing gas chromatography that produces the sample in the form of one or more separated gaseous species; and
    means for producing Raman radiation, attached to said gas chromatography means, for receiving the gaseous sample,
    wherein said directing means directs the broadband coherent beam and the narrowband coherent beam to said Raman radiation producing means.

24. The apparatus defined by claim 17, wherein said means for producing a narrowband coherent beam comprises an injection seeded, near transform-limited Nd:YAG laser.

25. The apparatus defined by claim 17, wherein said means for producing a narrowband coherent beam comprises a Q-switched laser.

26. The apparatus defined by claim 17, further comprising:
    driving means for driving the production of the broadband coherent beam from said broadband coherent beam generating means; and
    wherein said directing means comprises means for splitting said narrowband coherent beam into first and second narrowband coherent beams, for directing the first narrowband coherent beam to said driving means, and for directing the second narrowband coherent beam to the sample.

27. The apparatus defined by claim 26, wherein said driving means comprises means for generating a backward-propagating, phase-conjugate beam of Raman radiation in response to receiving the first narrowband coherent beam.

28. The apparatus defined by claim 27, wherein said means for generating a backward-propagating, phase-conjugate beam of Raman radiation is tilted with respect to an optical axis along which the first narrowband coherent beam travels toward said means for generating a backward-propagating, phase-conjugate beam of Raman radiation.

29. The apparatus defined by claim 28, wherein said means for generating a backward-propagating, phase-conjugate beam or Raman radiation is tilted about 1 degree with respect to the optical axis.

30. The apparatus defined by claim 28, wherein said means for generating a backward-propagating, phase-conjugate beam of Raman radiation is tilled more than 0 degrees and less than 2.2 degrees with respect to the optical axis.

31. The apparatus defined by claim 17, wherein said broadband laser beam generating means comprises an optical parametric oscillator.

32. The apparatus defined by claim 31, wherein said optical parametric oscillator comprises two tiltable beta barium borate crystals that continuously emit broadband light in the range of 1100 to 1700 nm in response to receiving a driving pulse in the range of 10–130 mJ per pulse.

33. A method of generating the complete vibrational Raman spectra of a sample comprising the steps of:
    producing a narrowband coherent beam having a bandwidth of less than 1 wavenumber;
    generating a broadband coherent beam having a bandwidth of more than 3000 wavenumbers; and
    directing the narrowband coherent beam and the broadband coherent beam to a sample simultaneously to produce coherent Raman radiation scattered from the sample and comprising the complete vibrational Raman spectra of the sample with a spectral resolution of less than one wavenumber.

34. The method defined by claim 33, further comprising the step of using the narrowband coherent beam to generate the broadband coherent beam.

35. The method defined by claim 33, wherein said producing step comprises the step of producing the narrowband coherent beam with a laser to produce a narrowband laser beam.

36. The method defined by claim 33, wherein said producing step comprises the step of producing the narrowband coherent beam with an optical parametric oscillator laser to produce the narrowband coherent beam.

37. The method defined by claim 33, wherein said producing step produces a narrowband coherent beam having a bandwidth of about 0.003 wavenumbers.

38. The method defined by claim 33, wherein said generating step generates a broadband coherent beam having wavelengths from about 1100 nm to about 1700 nm.

39. The method defined by claim 33, further comprising the steps of:
    performing gas chromatography to produce the sample in the form of one or more separated gaseous species; and
    directing the broadband coherent beam and the narrowband coherent laser beam to the gaseous sample.

40. The method defined by claim 33, wherein said producing step is performed with an injection seeded, near transform-limited Nd:YAG laser.

41. The method defined by claim 33, wherein said producing step is performed with a Q-switched laser.

42. The method defined by claim 33, further comprising the steps of:
    causing the production of the broadband laser beam from a broadband laser beam source with a driving device;
    splitting the narrowband coherent beam into first and second narrowband coherent beams;
    directing the first narrowband coherent beam to the driving device; and
    directing the second narrowband coherent beam to the sample.

43. The method defined by claim 42, wherein said causing step comprises the step of generating a backward-propagating, phase-conjugate beam of Raman radiation with the driving device in response to the driving device receiving the first narrowband coherent beam.

44. The method defined by claim 43, wherein said causing step further comprises the step of tilting the driving device with respect to an optical axis along which the first narrow-band coherent beam travels toward the driving device.

45. The method defined by claim 44, wherein said tilting step comprises the step of tilting the driving device about 1 degree with respect to the optical axis.

46. The method defined by claim 44, wherein said tilting step comprises the step of tilting the driving device more than 0 degrees and less than 2.2 degrees with respect to the optical axis.

47. The method defined by claim 33, wherein said generating step comprises the step of generating the broadband coherent beam with an optical parametric oscillator.

48. A Raman cell for generating a driving pulse for a broadband coherent beam generator comprising:

a closed cell filled with gas that produces a backward-propagating, phase-conjugate, coherent Raman radiation beam of substantially circular cross-section and substantially uniform intensity in response to being irradiated with a coherent beam, wherein said closed cell has side walls, wherein said closed cell has a window through which the coherent beam can enter to irradiate the gas inside the closed cell, and wherein said closed cell is tilted with respect to the optical axis along which the coherent beam travels to the window so that the entire coherent beam enters the window and is focused on one of the side walls of said closed cell.

49. The Raman cell defined by claim 48, wherein said closed cell is tilted about 1 degree with respect to the optical axis.

50. The Raman cell defined by claim 48, wherein said closed cell is tilted more than 0 degrees and less than 2.2 degrees with respect to the optical axis.

51. The Raman cell defined by claim 48, wherein said closed cell produces a 683 nm beam of about 70 mJ in response to being irradiated by a 532 nm laser beam of about 200 mJ.

52. The Raman cell defined by claim 48, wherein said closed cell produces the backward-propagating, phase-conjugate, coherent Raman radiation beam of substantially circular cross-section and substantially uniform intensity in response to being irradiated with a coherent beam having a wavelength in the range of 531.7 nm to 532.3 nm.

53. The Raman cell defined by claim 48, wherein said closed cell produces the backward-propagating, phase-conjugate, coherent Raman radiation beam of substantially circular cross-section and substantially uniform intensity in response to being irradiated with a coherent beam having a wavelength of any value.

54. The Raman cell defined by claim 48, wherein said closed cell produces the backward-propagating, phase-conjugate, coherent Raman radiation beam of substantially circular cross-section and substantially uniform intensity in response to being irradiated with a coherent beam having a wavelength from 200 nm to 20,000 nm.

* * * * *

UNITED STATES PATENT AND TRADEMARK OFFICE
CERTIFICATE OF CORRECTION

PATENT NO. : 6,747,735 B2
DATED : June 8, 2004
INVENTOR(S) : Peter Chen et al.

It is certified that error appears in the above-identified patent and that said Letters Patent is hereby corrected as shown below:

Title page,
Item [57], ABSTRACT,
Line 12, "3000 wavenumber" should read -- 3000 wavenumbers --.

Column 3,
Line 27, "commercially" should read -- commercially available --.

Column 8,
Line 12, "a— 100 mm" should read -- a –100 mm --.

Column 9,
Line 57, "as the" should read -- as to --.

Column 11,
Line 54, "systems)." should read -- Systems). --.

Column 14,
Line 26, "tiling" should read -- tilting --.

Column 17,
Line 65, "104" should read -- $10^4$ -- .

Column 19,
Line 32, "chromatograp" should read -- chromatography --.

Column 22,
Line 15, "analogous" should read -- analogous to --.

Column 25,
Line 38, "chromater 194" should read -- chromator 194 --.
Line 42, "two dimensional or three" should read -- two-dimensional or three- -- .
Line 59, "Roman" should read -- Raman --.

UNITED STATES PATENT AND TRADEMARK OFFICE
CERTIFICATE OF CORRECTION

PATENT NO. : 6,747,735 B2
DATED : June 8, 2004
INVENTOR(S) : Peter Chen et al.

It is certified that error appears in the above-identified patent and that said Letters Patent is hereby corrected as shown below:

Column 26,
Line 2, "lasers." should read -- laser. --.
Line 5, "hewn" should read -- beam --.

Column 27,
Line 14, "at" should read -- of --.
Line 61, "or" should read -- of --.

Signed and Sealed this

Thirtieth Day of November, 2004

JON W. DUDAS
*Director of the United States Patent and Trademark Office*